US010765299B2

(12) United States Patent
Ito et al.

(10) Patent No.: US 10,765,299 B2
(45) Date of Patent: Sep. 8, 2020

(54) FUTURE SHAPE ESTIMATION APPARATUS, INSERTION/REMOVAL SYSTEM, INSERTION/REMOVAL SUPPORT SYSTEM, FUTURE SHAPE ESTIMATION METHOD, AND RECORDING MEDIUM NON-TRANSITORY STORING FUTURE SHAPE ESTIMATION PROGRAM

(71) Applicant: OLYMPUS CORPORATION, Tokyo (JP)

(72) Inventors: Takeshi Ito, Hino (JP); Jun Hane, Tokyo (JP); Hiromasa Fujita, Hachioji (JP); Ryo Tojo, Hachioji (JP)

(73) Assignee: OLYPMUS CORPORATION, Tokyo (JP)

( * ) Notice: Subject to any disclaimer, the term of this patent is extended or adjusted under 35 U.S.C. 154(b) by 483 days.

(21) Appl. No.: 15/627,687

(22) Filed: Jun. 20, 2017

(65) Prior Publication Data
US 2017/0303769 A1    Oct. 26, 2017

Related U.S. Application Data

(63) Continuation of application No. PCT/JP2015/052696, filed on Jan. 30, 2015.

(51) Int. Cl.
*A61B 1/00* (2006.01)
*A61B 5/06* (2006.01)
(Continued)

(52) U.S. Cl.
CPC .......... *A61B 1/00013* (2013.01); *A61B 1/005* (2013.01); *A61B 1/00009* (2013.01);
(Continued)

(58) Field of Classification Search
CPC combination set(s) only.
See application file for complete search history.

(56) References Cited

U.S. PATENT DOCUMENTS 10,502,693 B2 * 12/2019 Tojo ................... G01D 5/35345
10,571,253 B2 *  2/2020 Sato ....................... G02B 23/24
(Continued)

FOREIGN PATENT DOCUMENTS

CN    102421349 A    4/2012
CN    103607946 A    2/2014
(Continued)

OTHER PUBLICATIONS

Japanese Office Action dated May 8, 2018 in Japanese Patent Application No. 2016-571643.
(Continued)

*Primary Examiner* — Timothy J Neal
*Assistant Examiner* — Jae Woo
(74) *Attorney, Agent, or Firm* — Scully Scott Murphy & Presser

(57) ABSTRACT

A future shape estimation apparatus includes an insertion section, a shape sensor and an insertion section future shape estimation circuit. The insertion section has flexibility and is to be inserted into an observation target object. The shape sensor detects a bending state of the insertion section and outputs a detection signal. The insertion section future shape estimation circuit estimates a future shape of the insertion section after a predetermined lapse of time based on information acquired from the detection signal output from the shape sensor, and outputs the future shape as future estimation shape information.

18 Claims, 17 Drawing Sheets

(51) Int. Cl.
*A61B 1/005* (2006.01)
*G02B 23/24* (2006.01)

(52) U.S. Cl.
CPC ........ *A61B 1/00022* (2013.01); *A61B 1/0051* (2013.01); *A61B 5/065* (2013.01); *G02B 23/2415* (2013.01)

(56) References Cited

U.S. PATENT DOCUMENTS

| | | | | |
|---|---|---|---|---|
| 2011/0184690 | A1* | 7/2011 | Iida | A61B 1/00158 702/150 |
| 2013/0261392 | A1* | 10/2013 | Yamamoto | G02B 23/2476 600/117 |
| 2013/0303878 | A1* | 11/2013 | Nevo | A61B 5/062 600/409 |
| 2015/0305597 | A1* | 10/2015 | Ito | A61B 6/12 600/424 |
| 2016/0360951 | A1* | 12/2016 | Hane | A61B 1/00004 |
| 2017/0100196 | A1* | 4/2017 | Takayama | A61B 34/20 |
| 2017/0245746 | A1* | 8/2017 | Komazaki | A61B 1/0051 |

FOREIGN PATENT DOCUMENTS

| | | |
|---|---|---|
| JP | 2007-044412 A | 2/2007 |
| JP | 2014-502911 A | 2/2014 |
| JP | 2014-113352 A | 6/2014 |
| WO | WO 2010/103866 A1 | 9/2010 |

OTHER PUBLICATIONS

Chinese Office Action dated Jun. 28, 2018 in Chinese Patent Application No. 201580072569.1.
German Office Action dated Jun. 15, 2018 in German Patent Application No. 11 2015 006 093.6.
International Search Report dated Apr. 28, 2015 issued in PCT/JP2015/052696.
English translation of International Preliminary Report on Patentability dated Aug. 10, 2017 together with the Written Opinion received in related International Application No. PCT/JP2015/052696.
Japanese Office Action dated Nov. 20, 2018 in Japanese Patent Application No. 2016-571643.

* cited by examiner

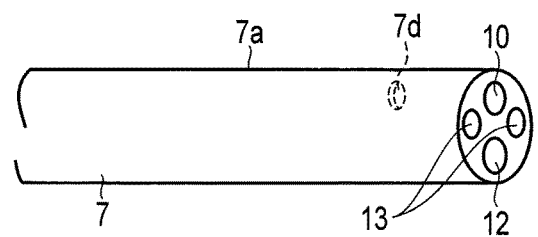
F I G. 2
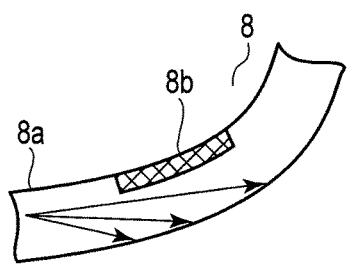
F I G. 3A
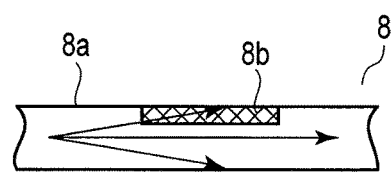
F I G. 3B
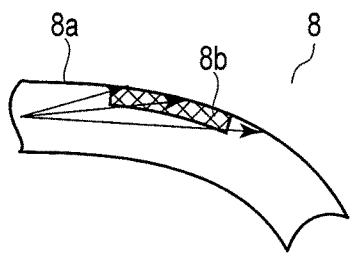
F I G. 3C

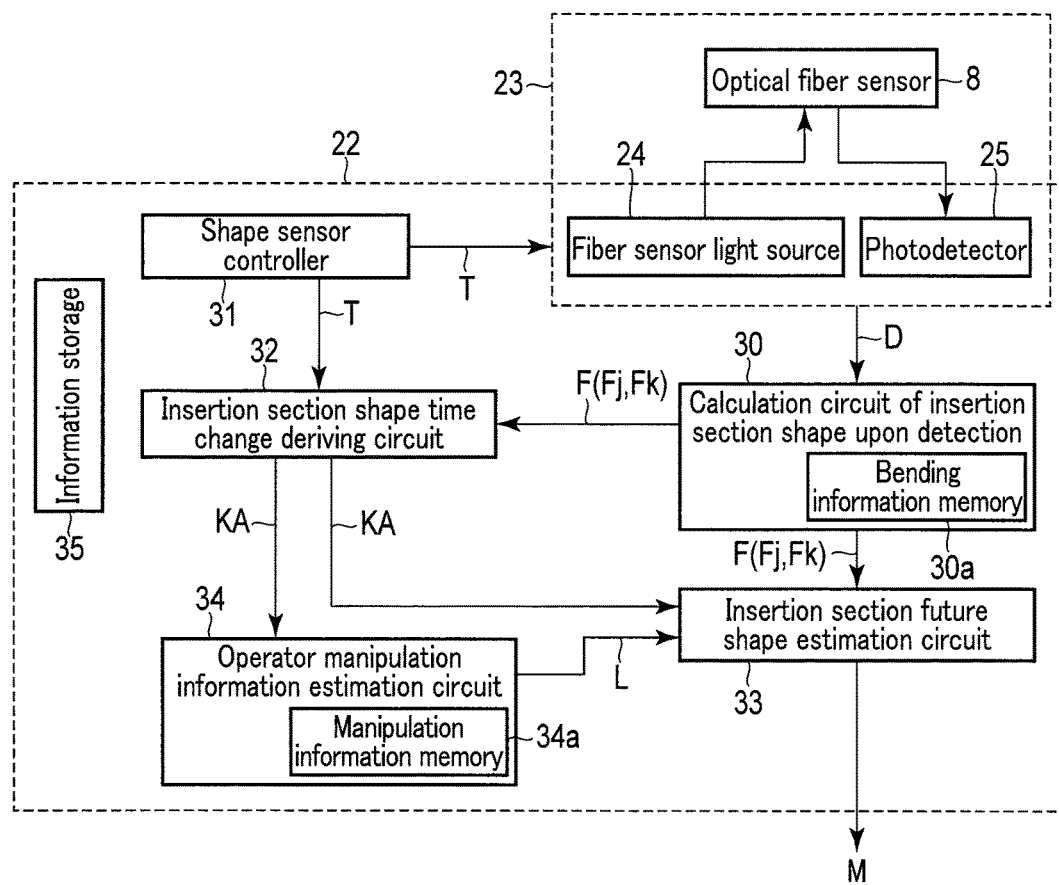
F I G. 4

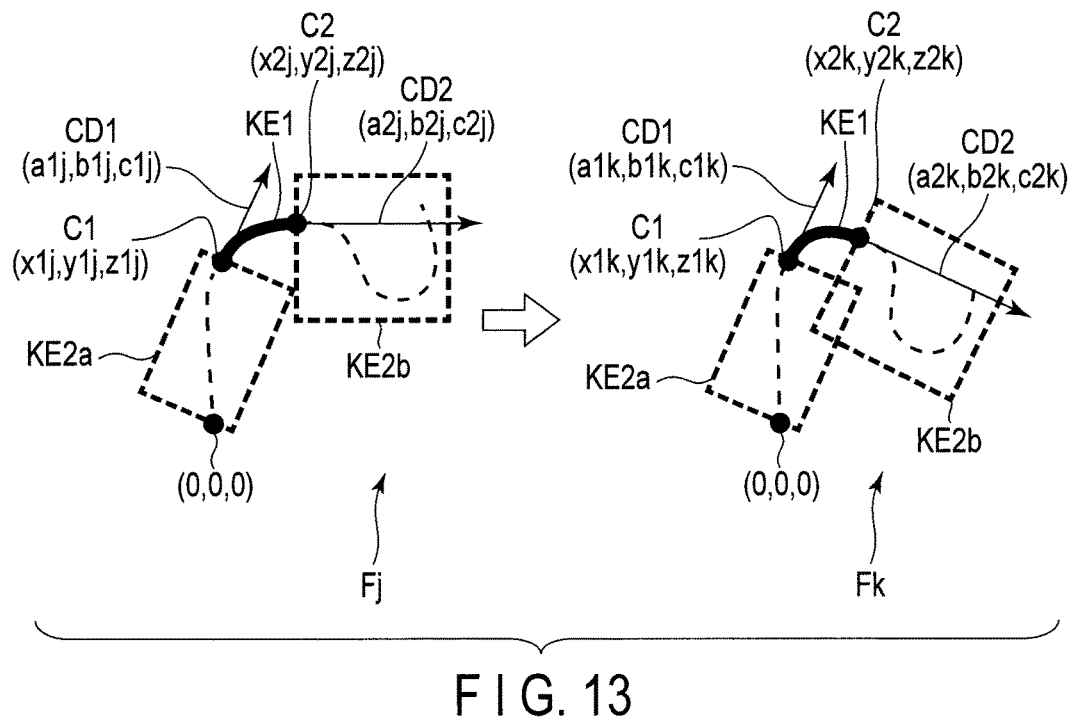
F I G. 13
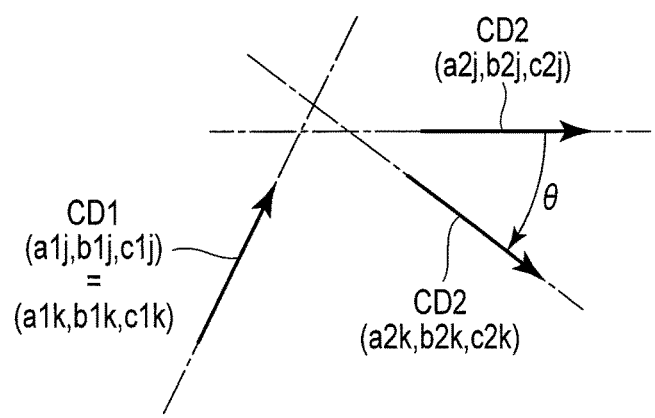
F I G. 14

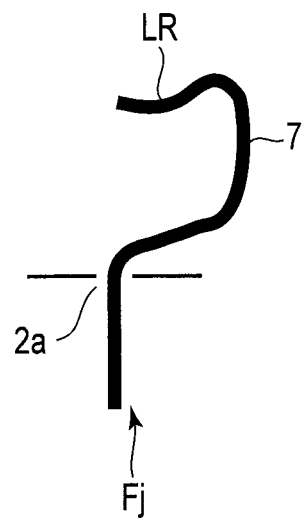
F I G. 17A
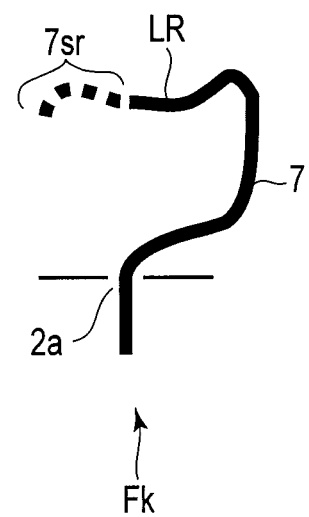
F I G. 17B

FUTURE SHAPE ESTIMATION APPARATUS, INSERTION/REMOVAL SYSTEM, INSERTION/REMOVAL SUPPORT SYSTEM, FUTURE SHAPE ESTIMATION METHOD, AND RECORDING MEDIUM NON-TRANSITORY STORING FUTURE SHAPE ESTIMATION PROGRAM

CROSS-REFERENCE TO RELATED APPLICATIONS

This application is a Continuation Application of PCT Application No. PCT/JP2015/052696, filed Jan. 30, 2015, the entire contents of which are incorporated herein by reference.

BACKGROUND OF THE INVENTION

1. Field of the Invention

The present invention relates to a future shape estimation apparatus, an insertion/removal system, an insertion/removal support system, a future shape estimation method, and a recording medium non-transitory storing a future shape estimation program for estimating a future shape of an insertion section to be inserted into an observation target object.

2. Description of the Related Art

There is an apparatus for performing an operation inside an observation target object by inserting an insertion section into the observation target object through a thin tube hole. For example, an endoscope is intended to observe the inner surface of an observation target object by inserting an insertion section into the observation target object. An apparatus such as the endoscope makes it impossible to observe, e.g. the shape of an insertion section in a tube hole directly from the outside.

More specifically, in the endoscope, the state of the insertion section, such as the position and shape thereof, in the observation target object cannot be seen from outside the observation target object. Thus, an operator needs to make an observation while imagining where in the tube hole the insertion section is located and what is observed at the present time regarding the state of the insertion section inserted into the tube hole. In short, an operator needs to manipulate the insertion section by intuition while imagining the state of the insertion section inside the observation target object.

As is seen from the above, when the shape of a tube hole is complex or when an observation target object is soft and deformed like a living body, the insertion into the observation target object itself could be difficult. When a tube hole differs in position or shape from what an operator imagined, it is likely to exert an influence on the observation target object as a worst case. Therefore, the operator needs to improve his or her operation skill, such as long hours of training for operation and gaining of intuition and experience during the actual operation. In other words, if an operator is not a highly-trained technician or expert, he or she could not insert the insertion section into the observation target object or perform an operation in the observation target object.

Under the circumstances described above, a technique of notifying an operator of the state of an insertion section in a tube hole is devised. For example, Jpn. Pat. Appln. KOKAI Publication No. 2007-044412 discloses an endoscope insertion shape probe for detecting a shape of an insertion section of an endoscope and displaying it. The endoscope insertion shape detection probe is inserted into a forceps channel provided in an endoscope apparatus to detect the shape of the insertion section of the endoscope. The endoscope insertion shape detection probe irradiates a mirror with light supplied from a light supply fiber and transmits the light reflected by the mirror through a plurality of curvature detection optical fibers. Each of the curvature detection optical fibers is provided with one optical loss section that varies in optical loss according to a corresponding curvature. Accordingly, the light guided by each of the curvature detection optical fibers reaches a module via the optical loss section. It is thus possible to detect the curvature of a curvature detection optical fiber in a position where the optical loss section is provided, by detecting a change of intensity of the light guided to the module.

Jpn. Pat. Appln. KOKAI Publication No. 2007-044412 also discloses using a plurality of curvature detection fibers whose optical loss sections are provided in different positions to detect the curvatures of the curvature detection fibers at the different positions of the optical loss sections, respectively. It is thus possible to detect the shape of an endoscope insertion section in accordance with the bending angle at a point where each optical loss section is provided and the distance between adjacent points.

BRIEF SUMMARY OF THE INVENTION

According to a first aspect of the present invention, there is provided a future shape estimation apparatus including an insertion section with flexibility which is to be inserted into an observation target object, a shape sensor which detects a bending state of the insertion section and outputs a detection signal, and an insertion section future shape estimation circuit which estimates a future shape of the insertion section after a predetermined lapse of time based on information acquired from the detection signal output from the shape sensor, and outputs the future shape as future estimation shape information.

According to a second aspect of the present invention, there is provided an insertion/removal system including an insertion section with flexibility which is to be inserted into an observation target object, a shape sensor which detects a bending state of the insertion section and outputs a detection signal a control section which performs a bending manipulation of the insertion section, and an insertion section future shape estimation circuit which estimates a future shape of the insertion section after a predetermined lapse of time based on information acquired from the detection signal output from the shape sensor, and outputs the future shape as future estimation shape information.

According to a third aspect of the present invention, there is provided an insertion/removal system including an insertion section with flexibility which is to be inserted into an observation target object, a shape sensor which detects a bending state of the insertion section and outputs a detection signal a control section which performs a bending manipulation of the insertion section, an insertion section future shape estimation circuit which estimates a future shape of the insertion section after a predetermined lapse of time based on information acquired from the detection signal output from the shape sensor, and outputs the future shape as future estimation shape information, and an operation support circuit which notifies future estimation shape information output from the insertion section future shape estimation circuit to support insertion/removal of the insertion section into/from the observation target object.

According to a fourth aspect of the present invention, there is provided a future shape estimation method including detecting a bending state of a flexible insertion section to be inserted into an observation target object by a shape sensor and outputting a detection signal, and estimating a future shape of the insertion section after a predetermined lapse of time based on information acquired from the detection signal output from the shape sensor, and outputting the future shape as future estimation shape information.

According to a fifth aspect of the present invention, there is provided a recording medium non-transitory storing a future shape estimation program causing a computer to perform an input function of inputting a detection signal output from a shape sensor which detects a bending state of a flexible insertion section to be inserted into an observation target object, and an insertion section future shape estimation function of estimating a future shape of the insertion section after a predetermined lapse of time based on information acquired from the detection signal input by the input function, and outputting the future shape as future estimation shape information.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a configuration diagram of a distal-end portion of an insertion section.

FIG. 3A is an illustration of a light transmission amount used when an optical fiber sensor is bent toward a bending shape detector.

FIG. 3B is an illustration of a light transmission amount used when the optical fiber sensor is not bent.

FIG. 3C is an illustration of a light transmission amount used when the optical fiber sensor is bent toward the opposite side of the bending shape detector.

FIG. 4 is a configuration diagram showing a support information circuit.

FIG. 13 is an illustration of a shape of each of the shape changing regions of the endoscope insertion section at the time of generation of the j-th and k-th timing signals acquired by an insertion section shape time change deriving circuit in a first modification to the first embodiment of the present invention.

FIG. 14 is an illustration of a change of the shape changing region of the endoscope insertion section in a connection direction at the time of generation of each of the j-th and k-th timing signals.

FIG. 17A is an illustration of the j-th insertion section shape information Fj upon detection.

FIG. 17B is an illustration of the k-th insertion section shape information Fk upon detection.

DETAILED DESCRIPTION OF THE INVENTION

First Embodiment

A first embodiment of the present invention will be described below with reference to the drawings.

Figure 1:
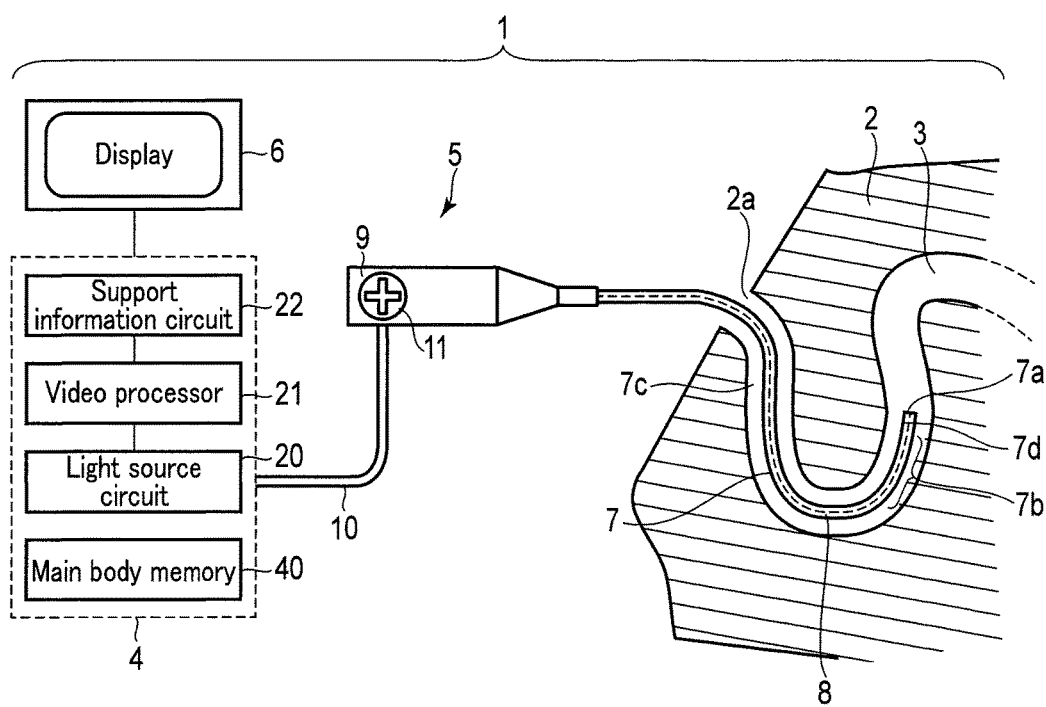
FIG. 1 is a configuration diagram of a first embodiment of an endoscope system as an insertion/removal system of the present invention.

FIG. 1 is a configuration diagram showing an endoscope system 1 as an insertion/removal system. This system 1 is used mainly to insert an endoscope insertion section (referred to as an insertion section hereinafter) 7 into an internal space (hollow) 3 of an observation target object 2 through an operator's operation to observe the inner surface of the internal space 3 of the observation target object 2.

The system 1 includes an endoscope main body 4, an endoscope unit 5 and a display 6 as configuration elements. The endoscope unit 5 includes the insertion section 7. The insertion section 7 is loaded with a shape sensor 8.

The configuration elements of the system 1 will be described.

[Endoscope Unit]

The endoscope unit 5 includes the insertion section 7, a control section 9 and a cable 10. The endoscope unit 5 is grasped and manipulated by an operator. By this manipulation, the insertion section 7 of the endoscope unit 5 is moved to an insertable position from an insertion opening 2a as an entrance portion of the observation target object 2 and inserted into the internal space 3 of the observation target object 2.

The cable 10 is intended to connect the endoscope unit 5 and the endoscope main body 4 and is detachable from the endoscope main body 4. One or more cables 10 may be connected between the endoscope unit 5 and the endoscope main body 4.

The insertion section 7 will be described specifically. The insertion section 7 is formed of a distal-end portion 7a and the other portion. The distal-end portion 7a includes a region formed hard (a hard portion). The other region of the distal-end portion 7a is formed flexibly. The hard portion of the distal-end portion 7a is formed in a preset region (a small region). In part of the flexible region of the insertion section 7, which is near the distal-end portion 7a, an active bending portion 7b is formed such that it can be bent actively. The active bending portion 7b can be bent actively in vertical and horizontal directions if an operator manipulates a control handle 11 provided in the control section 9. In the other region of the insertion section 7, a passive bending portion 7c is formed such that it can be bent passively. The passive bending portion 7c is bent passively after the shape of the observation target object 2. The passive bending portion 7c is bent passively depending on the way of operator's grasping, the relationship in position between the insertion opening 2a for the observation target object 2 and the control section 9, or the like.

The control section 9 includes the control handle 11. The operator manipulates the control handle 11 to bend the active bending portion 7b of the insertion section 7 in a vertical or horizontal direction. For example, the operator grasps the control section 9 with his or her one hand to manipulate the control handle 11 and thus bend the active bending portion 7b of the insertion section 7 in a vertical or horizontal direction. Upon receiving the operator's manipulation of the control handle 11, the control section 9 allows the bending amount of the active bending portion 7b to vary in the insertion section 7.

A plurality of paired manipulation wires are provided between the insertion section 7 and the control handle 11. These manipulation wires are used for bending in a vertical direction and bending in a horizontal direction. These manipulation wires are formed like a loop, for example. When the control handle 11 turns, the manipulation wires move between the insertion section 7 and the control handle 11 to transmit the turn of the control handle 11 to the insertion section 7. Thus, the active bending portion 7b of the insertion section 7 is bent in the vertical or horizontal direction in accordance with the control amount of the control handle 11.

FIG. 2 is a configuration diagram of the distal-end portion 7a of the insertion section 7 in the system 1. The distal-end portion 7a of the insertion section 7 is provided with various members corresponding to the use of the endoscope, including an image sensor 7d, an objective lens 10, an instrument channel 12 and an illumination section 13. The objective lens 10 is optically connected to the image sensor 7d. The instrument channel 12 is an opening into which, e.g. forceps are inserted to perform various types of operation and treatment in the internal space 3 of the observation target object 2. The illumination section 13 emits light from a light source circuit 20 of the endoscope main body 4 toward the internal space 3 of the observation target object 2.

In the system, 1, when the internal space 3 of the observation target object 2 is irradiated with the light emitted from the illumination section 13 of the insertion section 7, the light is reflected by the internal space 3 of the observation target object 2 and enters the objective lens 10. The image sensor 7d is provided at the distal-end portion 7a of the insertion section 7 to pick up an image of light incident upon the objective lens 10 and then output an imaging signal. This imaging signal is sent to a video processor 21 through the cable 10. The video processor 21 processes the imaging signal output from the image sensor 7d to acquire an observation image of the inner surface of the observation target object 21. This observation image is displayed on the display 6.

The insertion section 7 includes the active bending portion 7b bent by the manipulation of the control handle 11 and the passive bending portion 7c bent passively. The passive bending portion 7c is pushed against the wall surface of the internal space 3 of the observation target object 2 and thus bent after the shape of the wall surface of the internal space 3. If, therefore, the insertion section 7 is inserted into the internal space 3 of the observation target object 2, it moves in the internal space 3 of the observation target object 2 while being pushed against the wall surface of the internal space 3. The internal space 3 of the observation target object 2 may include introduction channels of, e.g. different shapes depending on, e.g. the type of the observation target object 2. The insertion section 7 therefore has a configuration capable of moving in the internal space 3 of the observation target object 2.

In the insertion section 7, the shape sensor 8 is provided to detect the entire shape of the insertion section 7. The shape sensor 8 is, for example, an optical fiber sensor (which will be described as an optical fiber sensor 8 hereinafter). In the optical fiber sensor 8, a plurality of detection points are so provided that they can detect the entire shape of the insertion section 7.

The detection points are light absorbers (referred to as bending shape detectors) 8b provided in an optical fiber 8a that forms the optical fiber sensor 8, as shown in FIGS. 3A to 3C, for example. The detection points are arranged and distributed in the longitudinal direction of the optical fiber sensor 8 over almost the entire length of the insertion section 7. The configuration and principle of the optical fiber sensor 8 will be described later.

The insertion section 7 and the control section 9 are mechanically connected to each other. The control section 9 and the cable 10 are also mechanically connected to each other.

[Endoscope Main Body]

The endoscope main body 4 includes the light source circuit 20, the video processor 21, a support information circuit 22 and a main body memory 40, as shown in FIG. 1. The light source circuit 20 includes lamps such as a xenon lamp and a halogen lamp or semiconductor light sources such as an LED and a laser. Furthermore, a member that allows light to be guided, such as a light guide, is provided to be inserted through the cable 10, the control section 9 and the insertion section 7. Accordingly, when the light source circuit 20 emits light, the light is emitted as illumination light from the illumination section 13 provided at the distal-end portion 7a of the insertion section 7, through the light guide or the like. The illumination light enters the observation target object 2 to illuminate the inside of the observation target object 2.

The video processor 21 processes an imaging signal output from the image sensor 7d mounted at the distal-end portion 7a of the insertion section 7 to acquire an observation image of the inner surface of the observation target object 2. The imaging signal output from the image sensor 7d is transmitted to the video processor 21 through the insertion section 7, the control section 9, and a signal line provided inside the cable 10. The video processor 21 converts the acquired observation image into an observation image signal that can be displayed on the display 6, and transmits the observation image signal to the display 6.

The main body memory 40 stores in advance information about the observation target object 2 and information about an observation operation to observe the observation target object 2. The main body memory 40 also stores future estimate shape information M output from the support information circuit 22.

FIG. 4 is a block diagram of the support information circuit 22. The support information circuit 22 includes part of a shape sensor circuit 23. The shape sensor circuit 23 includes the optical fiber sensor 8, a fiber sensor light source 24 and a photodetector 25.

Incidentally, the fiber sensor light source 24 and photodetector 25 are included in the support information circuit 22, and the optical fiber sensor 8 is not included in the support information circuit 22. The shape sensor circuit 23 outputs a detection signal D indicating optical information corresponding to the bending shape of the insertion section 7. The configuration and operation of the shape sensor circuit 23 will be described in detail later. The optical information corresponding to the bending shape of the insertion section 7 represents light intensity corresponding to the bending angle of optical fibers disposed in the optical fiber sensor 8.

The support information circuit 22 functions as an operation support circuit for supporting the insertion/removal of the insertion section 7 into/from the observation target object 2. More specifically, the support information circuit 22 receives the detection signal D from the shape sensor circuit 23, processes the detection signal D, and outputs support information for supporting operator's operation and manipulation, or future estimate shape information M indicating that the future shape of the insertion section 7 is estimated. The support information circuit 22 includes a calculation circuit of insertion section shape upon detection (referred to as a shape calculator hereinafter) 30, a shape sensor controller 31, an insertion section shape time change deriving circuit (referred to as a change deriving circuit hereinafter) 32, an insertion section future shape estimation circuit (referred to as a future shape estimator hereinafter) 33, an operator manipulation information estimation circuit (referred to as a manipulation estimator hereinafter) 34, and an information storage 35.

Incidentally, the fiber sensor light source 24 and the photodetector 25 which are part of the shape sensor circuit 23, are included in the support information circuit 22. The shape sensor circuit 23 includes a signal processing circuit (not shown) for processing the output signal of the photodetector 25 and outputting the detection signal D.

The shape calculator 30 processes the detection signal D output from the shape sensor circuit 23 to calculate the bending direction and magnitude of the insertion section that is bent, and outputs a result of the calculation as information of insertion section shape upon detection (referred to as insertion section shape information hereinafter) F. Here, the insertion section 7 is often bent because the portion other than the distal-end portion 7a is formed flexibly. Further, the insertion section 7 is hardly disposed linearly because the internal space 3 of the observation target object 2 is also complicated and bent. Therefore, the shape calculator 30 is described as intended not to simply calculate the shape of the insertion section 7 but to calculate the bending direction and magnitude of the insertion section 7 that is bent.

The shape calculator 30 includes a bending information memory 30a. The bending information memory 30a stores information indicating the relationship between the bending angle of the insertion section 7 and the variation of optical information represented by the detection signal D output from the shape sensor circuit 23. The bending information memory 30a also stores information about the number of detection points of the optical fiber sensor 8, the arrangement positions of the detection points and the directions (X direction and Y direction) of bending to be detected by the detection points. Therefore, the shape calculator 30 calculates the bending direction and magnitude of the insertion section 7 that is bent, based on the detection signal D output from the shape sensor circuit 23 and the information stored in the information memory 30a and outputs a result of the calculation as the insertion section shape information F.

The shape sensor controller 31 outputs a timing signal T to take timing with which the shape sensor circuit 23 detects a bending shape of the insertion section 7. The timing signal T is a square wave that becomes a high level in a fixed period, for example. When j and k are different natural numbers of n or less (n is a natural number of 2 or more), if j is smaller than k (j<k), the shape sensor controller 31 outputs timing signal T of square wave that become a high level with the first to n-th timings. The first to n-th timing of the timing signal T include a j-th timing and a k-th timing. Hereinafter, the timing signal when the high level is reached at a n-th timing is referred to as a n-th timing signal T.

The change deriving circuit 32 receives the timing signal T from the shape sensor controller 31, receives insertion section shape information F (referred to as the j-th insertion section shape information Fj hereinafter) from the shape calculator 30 when a j-th timing signal T is generated, and receives insertion section shape information F (referred to as the k-th insertion section shape information Fk hereinafter) from the shape calculator 30 when the k-th timing signal T is generated.

The change deriving circuit 32 compares the j-th insertion section shape information Fj and k-th insertion section shape information Fk which are received from the shape calculator 30. For convenience's sake, the j-th insertion section shape information Fj represents the j-th insertion section shape upon detection. Similarly, for convenience's sake, the k-th insertion section shape information Fk represents the k-th insertion section shape upon detection.

The change deriving circuit 32 analyzes a change in shape of the insertion section 7 during the period from the generation of the j-th timing signal T to the generation of the k-th timing signal T, based on a result of the comparison, and outputs the analysis result as insertion section shape time change information (referred to as shape change information hereinafter) KA. The shape change information KA will be described in detail later.

The future shape estimator 33 receives the insertion section shape information F from the shape calculator 30 and receives the shape change information KA from the change deriving circuit 32 to estimate a future bending shape of the insertion section 7 based on the insertion section shape information F and the shape change information KA from the current timing to the next timing. The future shape estimator 33 outputs the future bending shape of the insertion section 7 as future estimate shape information M.

To estimate a future shape of the insertion section 7, there is a case where an operator wishes to consider the insertion operation of the insertion section 7. In this case, the future shape estimator 33 receives operator manipulation information L from the manipulation estimator 34, together with the insertion section shape information F and the shape change information KA. The future shape estimator 33 estimates a future shape of the insertion section 7 on the basis of the combination of the insertion section shape information F, shape change information KA and operator manipulation information L, and outputs the estimated future shape as future estimate shape information M.

The manipulation estimator 34 receives the shape change information KA from the change deriving circuit 32 to estimate operator's manipulation based on the shape change information KA during the period from the generation of the j-th timing signal T to the generation of the k-th timing signal T and output the estimated operator's manipulation as operator manipulation information L. The operator manipulation information L will be described later. The manipulation estimator 34 includes a manipulation information memory 34a that stores handle control information indicating, e.g. the bending shape and the position of shape change of the insertion section when the control handle 11 is manipulated.

The information storage 35 stores the detection signal D output from the shape sensor circuit 23 and various items of information transmitted in the support information circuit 22, such as the insertion section shape information F, shape change information KA, operator manipulation information L and future estimate shape information M, in association with the timing signal T.

The information storage 35 stores information of correspondence between a plurality of detection points provided in the optical fiber sensor 8, namely position information items of the light absorbers 8a and the detection signal D indicating light intensity corresponding to the bending angle of the insertion section 7 and the bending angle of the optical fiber sensor 8.

The information storage 35 can exchange information with the shape calculator 30, the shape sensor controller 31, the change deriving circuit 32, the future shape estimator 33 and the manipulation estimator 34 in the support information circuit 22 through a channel not shown. The information stored in the information storage 35 can properly be read out by the operator. The information storage 35, main body memory 40, bending information memory 30a and manipulation information memory 34a may use storage areas of the same memory device in correspondence with one another. Common information can be stored in one of the main body memory 40, bending information memory 30a, manipulation information memory 34a and information storage 35 and can be read out of it through a channel not shown.

In this embodiment, the endoscopic main body 4 includes four units of the light source circuit 20, video processor 21, support information circuit 22 and main body memory 40. Without limiting to this, the endoscope main body 4 may include, for example, a printer. The endoscope main body 4 may also include medical equipment required for a variety of procedures and treatments and all the other devices connectable to the endoscope system 1.

The light source circuit 20, video processor 21 and support information circuit 22 function individually in the endoscope main body 4. Without limiting to this, the light source circuit 20, video processor 21 and support information circuit 22 may function as one processing unit in the endoscope main body 4. Some functions of the light source circuit 20 and video processor 21 can be incorporated in the support information circuit 22. Furthermore, the endoscope main body 4 can be formed integrally with a unit other than three units of the light source circuit 20, video processor 21 and support information circuit 22. The endoscope main body 4 can thus be combined freely, such as combined with another unit, taking into consideration various situations such as user's convenience and design easiness, and costs.

In the support information circuit 22, the functions of the shape calculator 30, shape sensor controller 31, change deriving circuit 32, future shape estimator 33 and manipulation estimator 34 can be integrated into one processing unit, one processing circuit or one computer processor.

In the support information circuit 22, each of the functions of the shape calculator 30, shape sensor controller 31, change deriving circuit 32, future shape estimator 33 and manipulation estimator 34 can be configured as an independent unit, an independent circuit or an independent computer processor.

The support information circuit 22 can be combined freely, such as combined with another unit, taking into consideration various situations such as user's convenience and design easiness, and costs.

[Display]

The display 6 can display the internal space 3 of the observation target object 2 to be observed by the system 1, information about the observation target object 2 which is previously stored in the main body memory 40 of the endoscope main body 4, information about an observation operation to observe the observation target object 2, and the future estimate shape information M output from the support information circuit 22. The display 6 includes a monitor display of liquid crystal, a CRT, an LED, plasma or the like. For convenience's sake, FIG. 1 shows one display 6, but the number of displays is not limited to one. Two or more displays can be arranged side by side or a plurality of displays can be arranged in different locations.

The display 6 is not limited only to displaying images and character information on the monitor display. The display 6 here is a general term of an output device using various information transmission techniques of informing an operator of information, including an output for aural recognition using voice, alarm sound or the like and an output for tactile recognition using vibration or the like.

[Shape Sensor 8]

In the optical fiber sensor (shape sensor) 8, as shown in FIGS. 3A to 3C, the bending shape detectors 8b are provided on part of the side of the elongated optical fiber 8a. The optical fiber sensor 8 used in this embodiment utilizes a phenomenon in which the intensity of light absorbed by the bending shape detectors 8b increases or decreases depending on the bending angle of the optical fiber 8a. If, therefore, the intensity of light absorbed by the bending shape detectors 8b increases depending on the bending angle of the optical fiber 8a in the optical fiber sensor 8, the intensity of light transmitted through the optical fiber 8a decreases. Accordingly, the optical fiber sensor 8 emits an optical signal with light intensity corresponding to the bending angle of the optical fiber 8a. The optical fiber sensor 8 includes, e.g. the optical fiber 8a as described above. If, therefore, the insertion section 7 is bent and accordingly the optical fiber 8a is bent, part of light transmitting through the optical fiber 8a leaks to the outside through the bending shape detectors 8b or is absorbed by the bending shape detectors 8b, thus decreasing the intensity of light transmitted through the optical fiber sensor 8. The bending shape detectors 8b are configured by removing part of a clad of the optical fiber 8a and then coating the removed part with a light-absorbing member or a coloring agent. In other words, the bending shape detectors 8b are provided on one side of the optical fiber 8a to reduce part of the light transmitted in accordance with the bending of the optical fiber 8a. That is, the bending shape detectors 8b change the optical characteristics of the optical fiber 8a, e.g. the light transmission amount thereof in accordance with the bending of the optical fiber 8a.

FIG. 3A is an image view a light transmission amount used when the optical fiber 8a is bent toward the bending shape detector 8b, FIG. 3B is an image view showing a light transmission amount used when the optical fiber 8a is not bent, and FIG. 3C is an image view showing a light transmission amount used when the optical fiber 8a is bent toward the opposite side of the bending shape detector 8b. As shown in these figures, the light transmission amount is the largest when the optical fiber 8a is bent toward the bending shape detector 8b, and it becomes smaller when the optical fiber 8a is not bent and much smaller when the optical fiber 8a is bent toward the opposite side of the bending shape detector 8b.

The optical fiber sensor 8 becomes a bending sensor by providing one bending shape detector 8b. The optical fiber sensor 8 can detect the entire three-dimensional shape of the insertion section 7 by providing a plurality of bending shape detectors 8b in the longitudinal direction and the circumferential direction of the insertion section 7.

The optical fiber sensor 8 may include, e.g. an optical means for attaching a different color agent to the bending shape detectors 8b and separating light in its wavelength. In the optical fiber sensor 8, therefore, a plurality of bending shape detectors 8b can be provided in a single optical fiber.

If a plurality of optical fibers including the bending shape detectors 8b are bound, a bend angle can be detected at a plurality of points. If the number of bending shape detectors 8b per optical fiber is increased, the number of optical fibers 8a can be decreased.

If a plurality of optical fibers 8a are bound, it is possible to enhance independence in detecting a bending angle of each optical fiber 8a by the bending shape detectors 8b of the optical fiber 8a. Accordingly, it is possible to improve detection accuracy for each of the bending shape detectors 8b and thus improve noise resistance.

The insertion section 7 includes the optical fiber sensor 8 such that a plurality of bending shape detectors 8b can be provided at given intervals, e.g. 10-cm intervals. If a plurality of bending shape detectors 8b are provided at these intervals, the overall bending shape of the insertion section 7 can be detected with high accuracy. If the interval between bending shape detectors 8b becomes longer than 10 cm, for example, the number of bending shape detectors 8b can be decreased to achieve cost reduction and simplify the system configuration for detecting the bending shape.

Incidentally, the insertion section 7 can be bent in an arbitrary direction by, e.g. an operator. To detect the bending shape of the insertion section 7 in three dimensions, for example, two or more bending shape detectors 8b have only to be provided in different circumferential directions in substantially the same location of the insertion section 7.

The shape sensor circuit 23 has a function of detecting a change in intensity of light guided to the optical fiber sensor 8 and includes the fiber sensor light source 24 and the photodetector 25. The optical fiber sensor 8 is provided in the insertion section 7. The fiber sensor light source 24 and the photodetector 25 are provided in the support information circuit 22.

The fiber sensor light source 24 emits detection light. The detection light emitted from the fiber sensor light source 24 is incident on the optical fiber sensor 8, guided by the optical fiber sensor 8 and then incident on the photodetector 25. At this time, the detection light passes through the bending shape detectors 8b provided in the optical fiber sensor 8. The photodetector 25 detects the incident light, and a signal processing circuit (not shown) converts the light intensity of the detected light into a detection signal D and outputs the detection signal D. The detection signal D is transmitted to the shape calculator 30. There is an optical fiber sensor 8 including, e.g. an optical means for attaching a color agent to the bending shape detectors 8b and separating light in its wavelength. When the optical fiber sensor 8 is used, the photodetector 25 separates the incident light in its wavelength, and the signal processing circuit (not shown) converts the light intensity of the separated light into a detection signal D and outputs the detection signal D.

[Operation of System]

An operation of the system 1 configured as described above will be described. The description of a basic operation of the existing endoscope system will be omitted.

If the system 1 is turned on by an operator, the shape sensor circuit 23 and the support information circuit 22 are also turned on. Accordingly, the shape sensor circuit 23 can detect a bending shape of the insertion section 7. Thus, the shape sensor circuit 23 sends to the shape sensor controller 31 a detectable signal (Ready signal) indicating that the shape of the insertion section 7 can be detected.

If the shape sensor controller 31 receives a detectable signal to recognize that the shape sensor circuit 23 is in a detectable state, it outputs first to n-th timing signals T in sequence. As for the first to n-th timing signals T, the first high-level signal is defined as a first timing signal, the next high-level signal is defined as a second timing signal, and the subsequent high-level signals are defined as the j-th, k-th, n-th (n=a natural number) timing signals. The intervals at which the first to n-th timing signals T are generated can be set as appropriate according to the contents of target support information, operator requests, operation speeds of the support information circuit 22 and the shape sensor circuit 23, etc. The first to n-th timing signals T may be generated periodically at regular intervals, or the intervals between the first to n-th timing signals may be changed according to circumstances.

The shape sensor circuit 23 receives the first to n-th timing signals T from the shape sensor controller 31. The photodetector 25 detects an optical signal which was output from the optical fiber sensor 8 in response to the first to n-th timing signals T and passed through the bending shape detectors 8b, and outputs a detection signal D corresponding to the optical signal. Regarding the operation of the optical fiber sensor 8, its description will be omitted because a publicly known operation can be used.

The shape sensor circuit 23 turns on power to cause the fiber sensor light source 24 to light up. The fiber sensor light source 24 emits detection light continuously with basically the same brightness and spectrum. The detection light is incident on the incident end of the optical fiber 8a of the optical fiber sensor 8. The optical fiber sensor 8 guides the detection light incident from the incident end of the optical fiber 8a and emits the detection light from the emission end of the optical fiber 8a through the bending shape detectors 8b provided in the optical fiber sensor 8. The light emitted from the emission end of the optical fiber 8a is incident on the light detector 25.

If the optical fiber sensor 8 is bent together with the insertion section 7, the intensity of light absorbed by the bending shape detectors 8b varies according to the bending angle of the optical fiber sensor 8. For example, as shown in FIG. 3A, the intensity of light absorbed by the bending shape detectors 8b decreases as the bending angle of the optical fiber 8a becomes larger toward the bending shape detectors 8b. Accordingly, the intensity of light transmitted through the optical fiber 8a increases. Thus, the optical fiber sensor 8 outputs an optical signal with light intensity corresponding to the bending angle of the insertion section 7. The optical signal output from the optical fiber sensor 8 is incident on the photodetector 25. The photodetector 25 receives the incident optical signal and converts it into an electrical signal, and the signal processing circuit outputs the electrical signal as a detection signal D corresponding to the light intensity of the optical signal.

The shape sensor circuit 23 sets a flag to the detection signal D so as to associate the optical signals from the bending shape detectors 8b provided in the optical fiber sensor 8 with the first to n-th timing signals T and distinguish among the optical signals from the bending shape detectors 8b. The detection signal D is transmitted to the shape calculator 30.

The shape calculator 30 receives the detection signal D with a flag from the shape sensor circuit 23 and calculates the bending direction and magnitude of the insertion section 7 that is bent for each of the first to n-th timing signals T by referring to position information of the bending shape detectors 8b stored in the information storage 35 and bending angle light intensity information indicating the relationship between the bending angle of the optical fiber and the detection signal D (light intensity), and then outputs them as the insertion section shape information F.

More specifically, the shape calculator 30 calculates the j-th insertion section shape information Fj on the basis of the detection signal D associated with, e.g. the j-th timing signal Tj among the first to n-th timing signals T1 to Tn. Similarly, the shape calculator 30 receives the detection signals D in sequence from the shape sensor circuit 23 for each of the k-th, l-th, . . . n-th (k-th to n-th) timing signals Tk, Tl, . . . Tn which are output in sequence from the shape sensor controller 31, and calculates the k-th to n-th insertion section shape information Fk to Fn for each of the k-th to n-th timing signals T. The k-th to n-th insertion section shape information Fk to Fn are stored in sequence in the information storage 35 in the support information circuit 22.

[Operation of Change Deriving Circuit 32]

The change deriving circuit 32 receives at least two items of insertion section shape information F of different timings output from the shape calculator 30 on the basis of the first to n-th timing signals T1 to Tn and compares these items of insertion section shape information F to derive shape change information KA.

Figure 5:
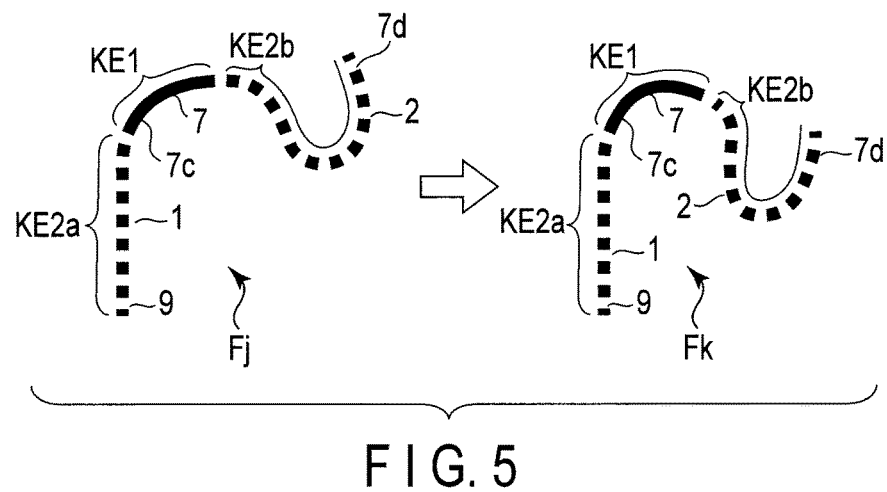
FIG. 5 is an illustration of the j-th and k-th insertion section shapes upon detection corresponding to the j-th and k-th timing signals calculated by a calculation circuit of insertion section shape upon detection.

The change deriving circuit 32 compares the j-th insertion section shape information Fj and the k-th insertion section shape information Fk calculated by the shape calculator 30 as shown in FIG. 5, for example.

As a result of the comparison, the change deriving circuit 32 extracts a region where the bending shape of the insertion section 7 is changed, as a shape changing region KE1 and extracts a region where the bending shape of the insertion section 7 is not changed, as first and second shape unchanging regions KE2a and KE2b.

If the j-th insertion section shape information Fj and the k-th insertion section shape information Fk shown in FIG. 5 are compared with each other, the bending shape of the first shape unchanging region KE2a close to the control section 9 in the insertion section 7 and the bending shape of the second shape unchanging region KE2b close to the distal-end portion 7a of the insertion section 7 do not change.

In the shape changing region KE1 between the first and second shape unchanging regions KE2a and KE2b, the bending shape of the insertion section 7 is changed.

In the first and second shape unchanging regions KE2a and KE2b, the bending shape of the insertion section 7 is not changed, but a relative positional relationship between the first and second shape unchanging regions KE2a and KE2b is changed. The relative positional relationship depends on the shape change of the shape changing region KE1 in the insertion section 7.

The change deriving circuit 32 calculates the classification of types of change in the bending shape of the extracted shape changing region KE1 and the amount of change in the bending shape in the shape changing region KE1. The insertion section 7 has substantially a circular section and is formed like an elongated rod with flexibility. It is thus considered that a partial change of the bending shape of the insertion section 7 includes two shape changes of, e.g. bending and torsion. It is also considered that a partial change of the bending shape of the insertion section 7 includes a case where bending and torsion are generated in combination, a case where bending and torsion are generated continuously in regions close to each other.

Figure 6:
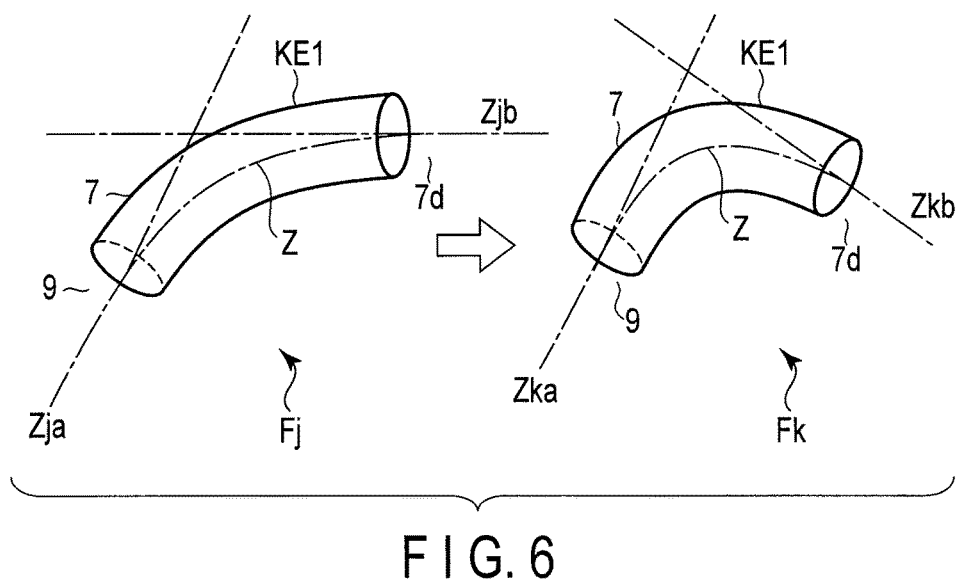
FIG. 6 is an illustration of an example of analyzing a shape changing region.

FIG. 6 shows an example of analyzing the shape changing region KE1, and shows an example of analyzing the shape changing region KE1 when the j-th timing signal Tj is generated and an example of analyzing the shape changing region KE1 when the k-th timing signal Tk is generated. The change deriving circuit 32 compares the bending shapes of the shape changing region KE1 at the time of generation of two timing signals, e.g. the j-th timing signal Tj and the k-th timing signal Tk. The j-th and k-th insertion section shape information Fj and Fk is three-dimensional information and thus the shape information of the shape changing region KE1 is also three-dimensional information.

As shown in FIG. 6, the change deriving circuit 32 sets the axial directions of both end portions of the shape changing region KE1, namely the axial directions Zja and Zjb of both end portions of the j-th insertion section shape information Fj and the axial directions Zka and Zkb of both end portions of the k-th insertion section shape information Fk, based on the j-th and k-th insertion section shape information Fj and Fk. Zja represents the j-th manipulation side central axis, and Zjb represents the j-th distal-end side central axis. Zka represents the k-th manipulation side central axis, and Zkb represents the k-th distal-end side central axis. Z represents the central axis of the insertion section 7 in the shape changing region KE1.

Figure 7:
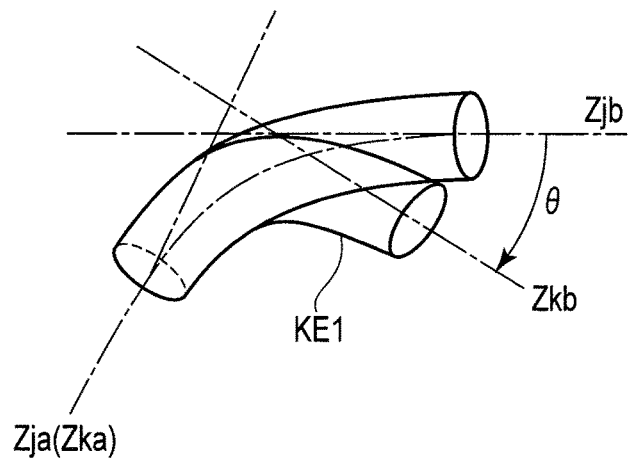
FIG. 7 is an illustration of a shape changing region KE1 when the j-th manipulation side central axis Zja and the k-th manipulation side central axis Zka are aligned with each other in the shape changing region shown in FIG. 6.

A region closest to the control section 9 in the shape changing region KE1 is connected to the shape unchanging region KE2 or directly connected to the control section 9. In this embodiment, it is connected to the first shape unchanging region KE2a. Thus, the type of change in the bending shape of the shape changing region KE1, the amount of change in the bending shape, and the direction of change in the bending are calculated based on the relationship in position between the j-th distal-end side central axis Zjb and the k-th distal-end side central axis Zkb when the j-th manipulation side central axis Zja and the k-th manipulation side central axis Zka are aligned with each other as shown in FIG. 7.

If the j-th and k-th manipulation side central axes Zja and Zka are aligned with each other, it is understood that the j-th and k-th distal-end side central axes Zjb and Zkb are moved in the same plane by bending of the insertion section 7. In this case, the shape changing region KE1 is bent by angle θ (referred to as a bending angle hereinafter) with regard to a portion at which the j-th and k-th manipulation side central axes Zja and Zka are aligned with each other. The angle θ corresponds to the amount of change in bending of the insertion section 7 during a period from the j-th to k-th timing signals T. In other words, since the j-th and k-th distal-end side central axes Zjb and Zkb are changed only in the same plane, it is understood that the insertion section 7 is not twisted but simply bent.

The amount and direction of change of the shape changing region KE1 can be calculated as the amount and direction of change of the bending angle. When the insertion section 7 is bent, the type of change is a change of the bending angle. The amount of change of the bending angle corresponds to the angle formed by the j-th and k-th distal-end side central axes Zjb and Zkb, namely angle θ, as shown in FIG. 7. The bending direction is a direction from the j-th distal-end side central axis Zjb to the k-th distal-end side central axis Zkb (clockwise direction) as indicated by the arrows.

The change deriving circuit 32 outputs information about the amount (angle θ) and direction (clockwise direction) of change in bending angle of the insertion section 7 as shape change information KA. The shape change information KA in this embodiment indicates that the type of change is bending in the plane, the amount of change is angle θ and the direction of change is clockwise. The shape change information KA is transmitted to the future shape estimator 33 and the manipulation estimator 34.

[Operation of Manipulation Estimator 34]

The manipulation estimator 34 estimates an operator's manipulation and outputs the estimated operator's manipulation as operator manipulation information L. Assuming a change in the bending shape of the insertion section 7 to be a result obtained by the operator's manipulation, the manipulation estimator 34 estimates an operator's manipulation performed during a period of, e.g. the j-th and k-th timing signals Tj and Tk on the basis of the shape change information KA and outputs the estimated operator's manipulation as operator manipulation information L. In this estimation, the type of the operator's manipulation, the direction of the manipulation and the amount of the manipulation are estimated. In other words, the operator manipulation information includes the type of the operator's manipulation, the direction of the manipulation and the amount of the manipulation.

The operator's manipulation is roughly divided into two manipulations of a control handle manipulation to manipulate the control handle 11 and a direct manipulation to manipulate the insertion section 7 by grasping it directly.

In the control handle manipulation, the control handle 11 is manipulated to bend the active bending portion 7b of the insertion section 7.

In the direct manipulation, an operator directly grasps a portion of the insertion section 7 that is not inserted into the internal space 3 of the observation target object 2 (a portion projected from the internal space 3 of the observation target object 2) to perform manipulations of push, removal, twist and the like.

The bending angle and bending direction of the insertion section 7 corresponding to the manipulation direction and manipulation amount of the control handle 11 manipulated by an operator is determined for each type of the endoscope unit 5 as handle manipulation information. The manipulation direction is, for example, the vertical direction and horizontal direction. The manipulation amount is a manipulation amount in the vertical direction and a manipulation amount in the horizontal direction. This handle manipulation information is stored in, for example, the manipulation information memory 34a provided in the manipulation estimator 34.

In the insertion section 7, there is a case where it is assumed that a bent portion is the active bending portion 7b and the bending shape of the active bending portion 7b is changed by an operator's manipulation of the control handle 11. In other words, there is a case where a change of the bending shape of the assumed active bending portion 7b and a change of the bending shape of the actually manipulated active bending portion 7b coincide with each other. In this case, it can be determined that the bending of the active bending portion 7b is changed by an operator's manipulation of the control handle 11.

If the shape changing region KE1 is the active bending portion 7b, the active bending portion 7b is bent actively in the vertical direction or the horizontal direction by manipulating the control handle 11 by an operator. However, there is a case where the shape change of the shape changing region KE1 does not coincide with the shape change made by the manipulation of the control handle 11. In this case, the manipulation estimator 34 estimates that it is caused by an operator's direct manipulation or a combined manipulation of an operator's direct manipulation and an operator's manipulation of the control handle 11.

In the example of a change in the bending shape of the insertion section 7 shown in FIG. 5, the operator's manipulation is determined as a direct manipulation because the shape changing region KE1 of the insertion section 7 is the passive bending portion 7c as described above. Since the direct manipulation is performed by directly grasping the control section 9 or a portion of the insertion section 7 projected from the internal space 3 of the observation target object 2, the force of the operator's manipulation is applied from the end portion of the shape changing region KE1 close to the control section 9.

Therefore, the manipulation estimator 34 estimates that the operator's manipulation capable of causing a change in the bending shape of the shape changing region KE1 is given from the control section 9 side.

If there is no change in the shape of the first and second shape unchanging regions KE2a and KE2b, the manipulation estimator 34 considers the absence of the change to estimate that the bending shape of the shape changing region KE1 is changed by the operator's manipulation.

In the example of a change in the bending shape of the insertion section 7 shown in FIG. 5, the shape of the first shape unchanging region KE2a is not changed during the period from generation of the j-th timing signal T until that of the k-th timing signal T. It is understood that the operator's manipulation force is transmitted to the end portion of the shape changing region KE1 close to the control section 9 without changing the shape of the first shape unchanging region KE2a.

Figure 8:
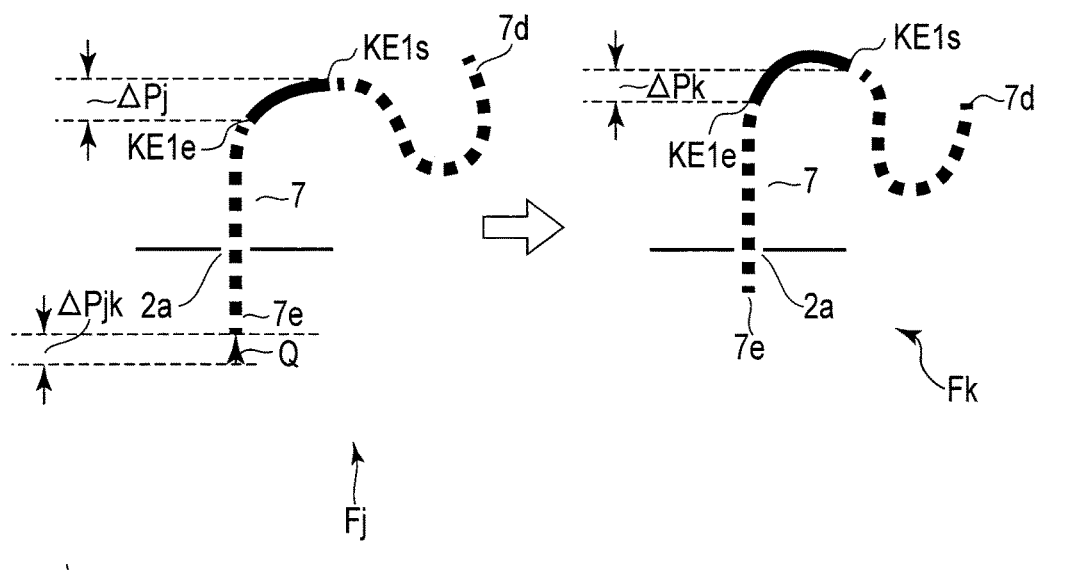
FIG. 8 is an illustration of a change in shape of an endoscope insertion section at the time of generation of each of the j-th and k-th timing signals.

Therefore, the manipulation estimator 34 can estimate that manipulation Q is applied to the insertion section 7 from the control section 9 side such that it is pushed in the axial direction of the insertion section 7, as shown in FIG. 8. FIG. 8 shows the j-th insertion section shape information Fj and the k-th insertion section shape information Fk manipulated by the operator.

The manipulation estimator 34 also estimates an approximate value of the amount of force of the operator's manipulation on the basis of information about hardness of the observation target object 2 stored in the information storage 35 and force required for bending based on the configuration of the insertion section 7. The configuration information about the configuration of the insertion section 7 is stored in, for example, the information storage 35. The configuration information includes information about easiness of partial bending based on the configuration of the insertion section 7 or easiness of bending for each bending direction, easiness of shape retaining of the insertion section 7, force required for bending the insertion section 7 and the like.

Next, it is verified whether the shape changing region KE1 is bent and deformed when an operator manipulates the insertion section 7. In this verification, the manipulation estimator 34 refers to the configuration information of the insertion section 7 stored in the information storage 35 and the other information such as physical information and shape information of the observation target object 2.

If, as a result of the verification, it is verified that the shape changing region KE1 is bent and deformed when an operator manipulates the insertion section 7, the manipulation estimator 34 determines the estimated operator's manipulation type, manipulation direction and manipulation amount as the type, direction and amount of manipulation performed by the operator during the period of the j-th timing signal Tj and k-th timing signal Tk, and outputs them to the future shape estimator 33 as operator manipulation information L.

The operator's manipulation type includes, for example, the push of the insertion section 7 into the internal space 3 of the observation target object 2. The manipulation direction includes a central axial direction of a portion of the insertion section 7 which is projected outside the internal space 3 of the observation target object 2 from the insertion opening 2a as shown in FIG. 8.

The manipulation amount is estimated from the positional relationship between the first and second shape unchanging regions KE2a and KE2b at the time of generation of each of the j-th and k-th timing signals Tj and Tk. The operation amount is estimated as a manipulation change amount $\Delta P$ ($=\Delta Pjk$) in the central axis direction of the insertion section 7 between the distal-end portion KE1s of the shape changing region KE1 and the end portion KE1e thereof close to the control section 9, as shown in FIG. 8.

Specifically, the manipulation estimator 34 estimates the difference $\Delta Pjk$ ($=\Delta Pj-\Delta Pk$) between the shape change amount $\Delta Pj$ in the direction of manipulation Q of the shape changing region KE1 in the j-th insertion section shape information Fj and the shape change amount $\Delta Pk$ in the direction of operation Q of the shape changing region KE1 in the k-th insertion section shape information Fk as an operator's manipulation changing amount $\Delta Pjk$, as shown in FIG. 8. The shape change amount $\Delta Pj$ in the j-th insertion section shape information Fj in this embodiment represents a change of the insertion section 7 projected outside the observation target object 2 from the insertion opening 2a in the central axis direction (the vertical direction in the drawing). Similarly, the shape change amount $\Delta Pk$ in the k-th insertion portion shape information Fk, represents a change in the central axis direction of the insertion section 7 on the outside of the observation target object 2 from the insertion opening 2a (the vertical direction in the drawing).

[Operation of Future Shape Estimator 33]

The future shape estimator 33 receives the insertion section shape information F (including Fj and Fk) from the shape calculator 30 and receives either one or both of the shape change information KA from the change deriving circuit 32 and the operator manipulation information L from the manipulation estimator 34.

The future shape estimator 33 calculates future estimate shape information M based on the insertion section shape information F and either one or both of the shape change information KA and the operator manipulation information L.

Here is a description of the calculation of the future estimate shape information M based on the insertion section shape information F and the shape change information KA.

A portion whose bending shape is deformed in the insertion section 7 is the shape changing region KE1 both ends of which are sandwiched between the first shape unchanging region KE2a and the second shape unchanging region KE2b, as shown in FIG. 5, for example.

The change deriving circuit 32 outputs the change amount of the bending angle and bending direction (clockwise direction) of the insertion section 7 in the shape changing region KE1 as the shape change information KA, as shown in FIG. 7.

The future shape estimator 33 receives the shape change information KA from the change deriving circuit 32 to estimate the insertion section future shape information M based on the change amount of the bending angle and bending direction (clockwise direction) of the insertion section 7 in the shape changing region as the shape change information KA.

Figure 9:
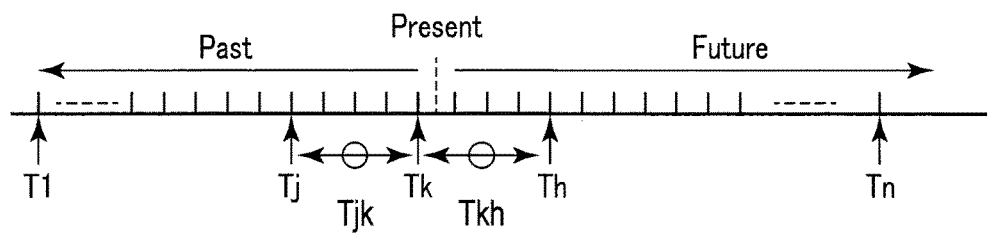
FIG. 9 is a chart showing an image of timing signal T output as time passes.

FIG. 9 shows an image of timing signal T (T1, Tj, Tk, Th, Tn) output as time passes from the past to the present and the future. In FIG. 9, h is a natural number that is larger than k. In the present, the shape sensor controller 31 has already output the j-th and k-th timing signals Tj and Tk and will output the h-th timing signal Th in the future. Here, time interval Tjk between the j-th and k-th timing signals Tj and Tk and time interval Tkh between the k-th and h-th timing signals Tk and Th are equal.

The future shape estimator 33 sets the first and second shape unchanging regions KE2a and KE2b unchanged in shape and sets the shape changing region KE1 being bent and deformed continuously at the same speed until the h-th timing signal Th is output. In accordance with this setting, the future shape estimator 33 estimates insertion section future shape information M (=Mh) at the time of generation of the h-th timing signal Th, as shown in FIG. 10.

Specifically, in the estimation of bending of the shape changing region KE1, the type of manipulation according to the shape change information KA is a bending manipulation, the direction of manipulation is a clockwise direction and the amount of manipulation is a bending angle θ during the period of the j-th and k-th timing signals Tj and Tk. The future shape estimator 33 estimates insertion section future shape information M (=Mh) at the time of generation of the h-th timing signal Th based on the bending angle of the type of manipulation, the clockwise direction of the direction of manipulation and the angle of the amount of manipulation.

Figure 10:
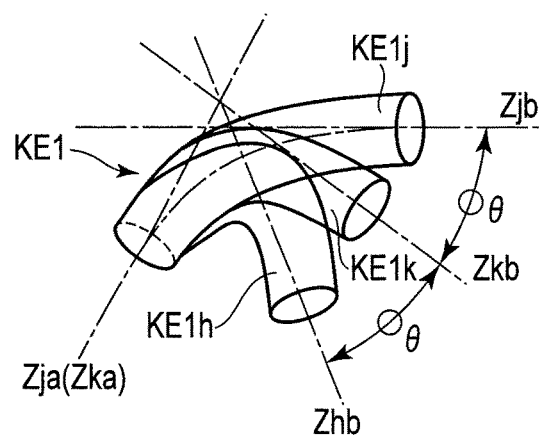
FIG. 10 is an illustration of a process of estimating future estimate shape information KE1$h$ of the shape changing region KE1 at the time of generation of the j-th to h-th timing signals T.

FIG. 10 illustrates a process of estimating future estimate shape information KE1h of the shape changing region KE1 at the time of generation of the j-th to h-th timing signals T. This figure illustrates a detection shape KE1j of the shape changing region KE1 at the time of generation of the j-th timing signal Tj, a detection shape KE1k of the shape changing region KE1 at the time of generation of the k-th timing signal Tk, and future estimate shape information KE1h of the shape changing region KE1 at the time of generation of the h-th timing signal Tj. As shown in FIG. 10, the bending angle of the shape changing region KE1 is estimated as being varied continuously at a constant change speed.

Figure 11:
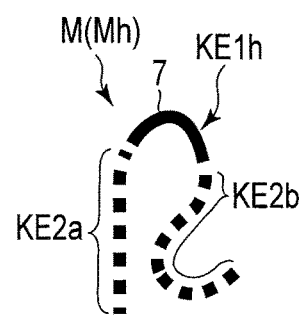
FIG. 11 is an illustration of insertion section future shape information (time change) Mh of the entire insertion section at the time of generation of the h-th timing signal estimated using insertion section shape time change information KA.

FIG. 11 shows insertion section future shape information (time change) Mh of the entire insertion section 7 at the time of generation of the h-th timing signal Th. The insertion section future shape information Mh includes the future estimate shape information KE1h of the shape changing region KE1 and the first and second shape unchanging regions KE2a and KE2b on both ends of the shape changing region KE1.

Below is a description of the calculation of the future estimate shape information M using the operator manipulation information L.

Figure 12:
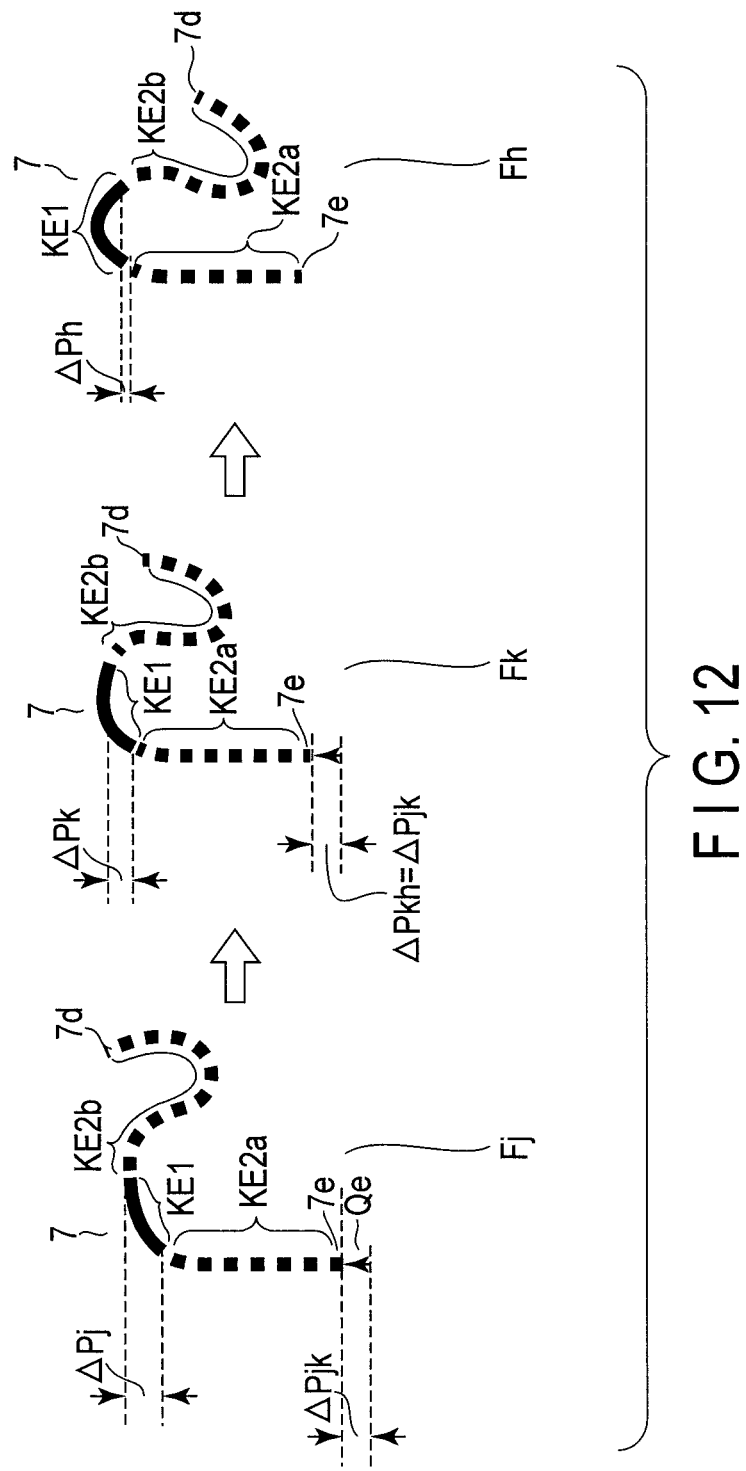
FIG. 12 is an illustration of each of the shapes of the endoscope insertion section taken by an operator's manipulation when the j-th, k-th and h-th timing signals are generated.

FIG. 12 illustrates changes of the shape of the endoscope insertion section 7 taken by generation of the j-th, k-th and h-th timing signals Tj, Tk, Th when an operator's manipulation is performed. In other words, it shows changes among the j-th insertion section shape information Fj, the k-th insertion section shape information Fk and the h-th insertion section shape information Fh.

As described in the foregoing paragraphs of [Operation of Manipulation Estimator 34], in the operator manipulation information L, for example, the manipulation type is a push, the manipulation direction is a central axial direction of the insertion section 7 projected outside the observation target object 2 from the insertion opening 2a, and the manipulation amount is an operator's manipulation changing amount ΔPjk.

The future shape estimator 33 estimates a future shape of the insertion section 7 at the time of generation of the future h-th timing signal Th on the basis of the operator manipulation information L. The estimation method is substantially the same as the method of calculating the future estimate shape information M based on the insertion section shape information F and the shape change information KA as described above.

In the estimation of the insertion section future shape information M, the future shape estimator 33 calculates the bending shape of the insertion section 7 taken when the manipulation type, manipulation direction and manipulation amount are continuously estimated, as the insertion section future shape information M.

Along with this, the future shape estimator 33 estimates the insertion section future shape information M on the assumption that the shape changing region KE1 is bent by the estimated operator's manipulation and the first and second shape unchanging regions KE2a and KE2b do not change in shape.

Specifically, like the above, the future shape estimator 33 estimates insertion section future shape information M (=Mh) at the time of generation of the h-th timing signal Th on the assumption that the manipulation type is a push, the manipulation direction is a central axial direction of the insertion section 7 projected outside the observation target object 2 from the insertion opening 2a, and the manipulation amount is an operator's manipulation changing amount ΔPjk shown in FIG. 8.

In this embodiment, as shown in FIG. 9, time interval Tjk between the j-th and k-th timing signals Tj and Tk and time interval Tkh between the k-th and h-th timing signals Tk and Th are equal.

Therefore, the future shape estimator 33 estimates that a manipulation changing amount ΔPkh that is predicted to be manipulated by an operator during the time interval Tkh between the k-th and h-th timing signals Tk and Th is equal to an operator's manipulation changing amount ΔPjk during the time interval Tjk between the j-th and k-th timing signals Tj and Tk (ΔPjk=ΔPkh) as shown in FIG. 12.

If, as shown in FIG. 12, the manipulation changing amount at the time of generation of the j-th timing signal Tj is ΔPjk, the shape changing amount at the time of generation of the k-th timing signal Tk is ΔPk and the shape changing amount at the time of generation of the h-th timing signal Th is ΔPh, the shape changing amount ΔPh is obtained by the following equation:

$$\Delta Ph = \Delta Pk - \Delta Pkh (=\Delta Pk - \Delta Pjk) \qquad (1)$$

Therefore, the future shape estimator 33 estimates the insertion section future shape information M (=Mh) at the time of generation of the h-th timing signal Th on the basis of the shape changing amount ΔPh at the time of generation of the h-th timing signal Th.

As shown in FIG. 12, the future shape estimator 33 uses the operator manipulation information L estimated by the manipulation estimator 34 to estimate a deforming shape in the shape changing region KE1 such that the shape deforming amount ΔPh in the shape deforming region KE1 of the insertion section 7 becomes the shape changing amount ΔPh shown in the above equation (1). In this embodiment, the deforming shape of the shape changing region KE1 is estimated considering the endoscope structure.

Then, the future shape estimator 33 compares the insertion section future shape information (time change) M and the insertion section future shape information (operator's manipulation) M to estimate the final insertion section future shape information M.

There are some methods for estimating the final insertion section future shape information M from two items of insertion section future shape information M of the insertion section future shape information (time change) M and the insertion section future shape information (operator's manipulation) M. For example, it is favorable to choose one of the two items of insertion section future shape information M using the other information such as information of the endoscope structure and observation target object 2 and the type of observation operation. A method for obtaining, e.g. the average of the two items of insertion section future shape information M is also favorable. In this case, it is favorable to obtain the average simply and it is favorable to take the weighted average in the light of the other information described above. It is also favorable to present an operator both of the two items of insertion section future shape information M.

In this embodiment, it is assumed that time interval Tjk between the j-th and k-th timing signals Tj and Tk and time interval Tkh between the k-th and h-th timing signals Tk and Th are equal to each other as shown in FIG. 9; however, the prediction is, of course, possible even though the time intervals Tjk and Tkh are not equal to each other.

As described above, the future shape estimator 33 assumes that the deformation in the shape deforming region KE1 of the insertion section 7 and operator's manipulation are performed at a constant speed during the period of the j-th and k-th timing signals Tj and Tk. Therefore, if, for example, the time intervals Tjk and Tkh each becomes half, the insertion section future shape information M has only to be estimated by representing the changing amount θ of the bending angle of the insertion section 7 as θ/2 and the manipulation amount as ΔPjk/2. If the ratio of elapsed time is obtained for the other timing in the same manner, the insertion section future shape information M can be estimated.

Advantageous Effect

As described above, according to the first embodiment, a shape of the insertion section 7 inserted into the internal space 3 of the observation target object 2 is estimated by the shape sensor circuit 23 to estimate a future shape of the insertion section 7 after elapsed time, e.g. Tkh from the k-th timing signal Tk to the h-th timing signal Th based on the sensed insertion section shape information F and then output it as future estimate shape information M. Thus, a future shape of the insertion section 7 to be taken from now on when an operator inserts the insertion section 7 into the internal space 3 of the observation target object 2 can be estimated. The estimated shape of the insertion section 7 can be displayed to the operator on, e.g. the display 6 as support information at the time of insertion of the insertion section 7. As a result, it is possible to make time required for operator's training and skill improvement shorter than in the conventional endoscope system. Even an inexperienced or low skill level operator can insert and remove the insertion section 7 into and from the internal space 3 of the observation target object 2 relatively easily.

In other words, an operator can determine that the insertion section 7 can continue to insert or remove if the estimated shape of the insertion section 7 is an operator's desired shape. On the other hand, the operator can determine that it is better to change the insertion or removal operation if the estimated shape of the insertion section 7 is not a desired shape. In the first embodiment, therefore, time required for operator's training and skill improvement can be made shorter than in the existing system. Even an inexperienced or low skill level operator can insert and remove the insertion section 7 relatively easily.

In the foregoing first embodiment, the change deriving circuit 32 compares two items of insertion section shape information F, namely the j-th insertion section shape information Fj and the k-th insertion section shape information Fk. Without limiting to this, the change deriving circuit 32 can compare three or more items of insertion section shape information F. For example, they include the j-th insertion section shape information Fj, the k-th insertion section shape information Fk and the l-th insertion section shape information Fl corresponding to the l-th timing signal T.

If three or more items of insertion section shape information F (Fj, Fk, Fl, etc.) are compared as described above, it is possible to acquire the states of change in shape of the insertion section 7, such as information as to whether the shape of the insertion section continues to change stably at a low speed, whether it changes with acceleration, and whether the manipulation is repeated, in addition to the foregoing advantageous effect of the first embodiment.

Taking into consideration that these three or more items of insertion section shape information F (Fj, Fk, Fl, etc.) are used, the manipulation estimator 34 can estimate the operator manipulation information L. This allows the future shape estimator 33 to estimate insertion section future shape information M with higher accuracy.

[First Modification to First Embodiment]

Next, a first modification to the first embodiment of the present invention will be described with reference to the drawings. In this modification, the same sections as those of the first embodiment will not be described, but only different sections will be described in detail.

[Operation of Insertion Section Shape Time Change Deriving Circuit of First Modification]

This modification differs in operation of the change deriving circuit 32 from the foregoing first embodiment.

In the first embodiment, the change deriving circuit 32 compares the j-th insertion section shape information Fj and the k-th insertion section shape information Fk calculated by the shape calculator 30 as shown in FIG. 5, and extracts a region in which the shape of the insertion section 7 is changed as the shape changing region KE1 and regions in which the shape of the insertion section 7 is unchanged as the first and second shape unchanging regions KE2a and KE2b, based on a result of the comparison.

In contrast to the above, in this modification, the change deriving circuit 32 focuses on the first and second shape unchanging regions KE2a and Ke2b extracted as regions in which the bending shape of the insertion section 7 is not changed and derives shape change information KA based on the relative positional relationship between the shape unchanging regions KE2a and Ke2b.

In this modification, the operation of calculating the insertion section shape information F by the shape calculator 30 and the operation of extracting the shape changing region KE1 and the first and second shape unchanging regions KE2a and KE2b by the change deriving circuit 32 are the same as those in the first embodiment.

Next is a description of some of the operations of the change deriving circuit 32 in this modification which differ from those in the first embodiment.

FIG. 13 is an illustration of the operation of the change deriving circuit 32. This figure illustrates a shape of the insertion section 7 at the time of generation of the j-th timing signal Tj acquired by the change deriving circuit 32 and a shape of the insertion section 7 at the time of generation of the k-th timing signal Tk acquired by the change deriving circuit 32.

The change deriving circuit 32 compares the j-th insertion section shape information Fj and k-th insertion section shape information Fk calculated by the calculation circuit of insertion section shape upon detection 30 and extracts the shape changing region KE1 in which the shape of the insertion section is changed and the first and second shape unchanging regions KE2a and KE2b in which the shape of the insertion section 7 is not changed.

As shown in FIG. 13, the insertion section 7 includes a first connecting portion C1 that connects the first shape unchanging region KE2a and the shape changing region KE1 and a second connecting portion C2 that connects the shape changing region KE1 and the second shape unchanging region KE2b.

The change deriving circuit 32 calculates the coordinates (connecting portion coordinates) of the first connecting portion C1 at the time point of generation of the j-th timing signal Tj and the time point of generation of the k-th timing signal Tk and a connection direction CD1 that is a tangential direction of the central axis of the insertion section 7 at the first connecting portion C1.

Along with this, the change deriving circuit 32 calculates the coordinates (connecting portion coordinates) of the second connecting portion C2 at the time point of generation of the j-th timing signal Tj and the time point of generation of the k-th timing signal Tk and a connection direction CD2 that is a tangential direction of the central axis of the insertion section 7 at the second connecting portion C2.

Here, any coordinate system representing the connecting portion coordinates of each of the first and second connecting portions C1 and C2 can be used if the j-th insertion section shape information Fj and the k-th insertion section shape information Fk can be compared with each other.

In this modification, the support information circuit 22 determines the positions of the j-th insertion section shape information Fj and k-th insertion section shape information Fk which are the nearest to the control section 9 as the origin coordinates (0,0,0). That is, the origin coordinates (0, 0, 0) are located at the end portion of the control section 9 of the first shape unchanging region KE2a.

Furthermore, in this modification, the support information circuit 22 calculates the connecting portion coordinates of the first and second connecting portions C1 and C2 based on the origin coordinates (0, 0, 0), the j-th insertion section shape information Fj and the k-th insertion section shape information Fk.

Next is a description of the coordinates of the first shape unchanging region KE2a at the time of generation of the j-th and k-th timing signals Tj and Tk.

The connecting portion coordinates C1 close to the distal end of the first shape unchanging region KE2a at the time of generation of the j-th timing signal Tj are represented by $(x1j, y1j, z1j)$ as shown in FIG. 13.

The connecting portion coordinates C1 close to the distal end of the first shape unchanging region KE2a at the time of generation of the k-th timing signal Tk are represented by $(x1k, y1k, z1k)$.

In this modification, the first shape unchanging region KE2a is present between a portion of the origin coordinates (0, 0, 0) and a portion of the connecting portion coordinates C1 and thus the connecting portion coordinates C1 $(x1j, y1j, z1j)$ and the connecting portion coordinate C1 $(x1k, y1k, z1k)$ are equal.

The connection direction CD1 is calculated as a vector indicating a connection direction of the first shape unchanging region KE2a and the shape changing region KE1.

The connection direction CD2 is calculated as a vector indicating a connection direction of the shape changing region KE1 and the second shape unchanging region KE2b.

In this modification, only information of the directions of the vectors of the connection directions CD1 and CD2 is necessary, not information of the length of the vectors. For this reason, in this modification, the vector of each of the connection directions CD1 and CD2 is determined as a unit vector of length "1."

The vector of the connection direction CD1 at the time of generation of the j-th timing signal Tj is represented by $(a1j, b1j, c1j)$ as shown in FIG. 13.

The vector of the connection direction CD1 at the time of generation of the k-th timing signal Tk is represented by $(a1k, b1k, c1k)$.

Since it is the first shape unchanging region KE2a that is connected to the origin coordinates (0, 0, 0), the vector $(a1j, b1j, c1j)$ of the connection direction CD1 at the time of generation of the j-th timing signal Tj and the vector $(a1k, b1k, c1k)$ of the connection direction CD1 at the time of generation of the k-th timing signal Tk in the first modification are equal.

Next, the coordinates of the second shape unchanging region KE2b at the time of generation of the j-th and k-th timing signals Tj and Tk are obtained in the same manner as the foregoing coordinates of the first shape unchanging region KE2a.

The connecting portion coordinates C2 close to the proximal end of the second shape unchanging region KE2b at the time of generation of the j-th timing signal Tj are represented by $(x2j, y2j, z2j)$ as shown in FIG. 13.

The connecting portion coordinates C2 close to the proximal end of the second shape unchanging region KE2b at the time of generation of the k-th timing signal Tk are represented by $(x2k, y2k, z2k)$.

The vector of the connection direction CD2 at the time of generation of the j-th timing signal Tj is represented by $(a2j, b2j, c2j)$.

The vector of the connection direction CD2 at the time of generation of the k-th timing signal Tk is represented by $(a2k, b2k, c2k)$.

Thus, the change deriving circuit 32 can represent information of the change in shape of the insertion section 7 by the positions and directions of the first and second shape unchanging regions KE2a and KE2b. In other words, the shape changing region KE1 is present between the first and second shape unchanging regions KE2a and KE2b. The information of the change in the shape of the insertion section 7 can be rewritten by only information of the coordinates $(x1j, y1j, z1j)$ of the first connecting portion C1 of the first shape unchanging region KE2a and the shape changing region KE1, the coordinates $(x2j, y2j, z2j)$ of the second connecting portion C2 of the second shape unchanging region KE2b and the shape changing region KE1, and the vectors CD1 and CD2 in the tangential direction of the insertion section 7 in these coordinates.

Incidentally, FIG. 13 is presented for the purpose of easily imaging a change in the shape of the insertion section 7. In this figure, the first and second shape unchanging regions KE2a and KE2b are each expressed by a dotted rectangle, and the shape changing region KE1 is expressed by a solid line corresponding to the bending shape. The change deriving circuit 32 need not generate or use information to express the shape changing and unchanging regions by a dotted rectangle and a solid line. In this modification, for convenience of description, a simple example where the shape changing region KE1 is present between the first and second shape unchanging region KE2a and KE2b is presented. Actually, there is a case where the shape changing region KE1 and one of the first and second shape unchanging regions KE2a and KE2b are repeated alternately. In this case, the first and second shape unchanging regions KE2a and KE2b include two position coordinates of the connecting portion coordinates close to the control section 9 and the connecting portion coordinates close to the distal end portion. However, in the first and second shape unchanging regions KE2a and KE2b, the shape of the insertion section 7 does not change. Even though the shape changing region KE1 and one of the first and second shape unchanging regions KE2*a* and KE2*b* are repeated alternately as described above, the entire shape of the insertion section 7 can be obtained with all timings if there are three information items indicated below. In other words, if the coordinates (first information item) close to the control section 9 in a shape unchanging region, the coordinates (second information item) close to the distal end of the insertion section 7 therein, the vector (third information item) in the connection direction close to the distal end thereof are known with a certain timing and any two of the first to third information items are known with another timing, the remaining one information item can be obtained by calculation.

Next, the change deriving circuit 32 calculates a type of the shape change of the shape changing region KE1, a direction of the shape change, and an amount of the shape change using information of the connection direction CD1 and connecting portion coordinates C1 on the control section 9 side at the time of generation of the j-th and k-th timing signals Tj and Tk. Specifically, the change deriving circuit 32 calculates a type of the shape change, a direction of the shape change, and an amount of the shape change from a relative arrangement relationship between the shape changing region KE1 and the first and second shape unchanging regions KE2*a* and KE2*b*. In other words, when the connecting portion coordinates C1 of the first shape unchanging region KE2*a* at the time of generation of the j-th and k-th timing signals Tj and Tk are equal to each other and so are the connection directions CD1, the change deriving circuit 32 can obtain a change in the connecting portion coordinates C2 and the connection directions CD2 of the second shape unchanging region KE2*b* to obtain a relative arrangement relationship between the shape changing region KE1 and the first and second shape unchanging regions KE2*a* and KE2*b*.

In this modification, since the first shape unchanging region KE2*a* does not move, the connecting portion coordinates C1 of the first shape unchanging region KE2*a* and the connection direction CD1 of the connecting portion C1 do not change but have an equal value.

Even though the shape changing region KE1 is present close to the control section 9, a type, a direction and an amount of change are calculated in this modification as the insertion section 7 side connection coordinates C2 and connection direction CD2 of the first and second shape unchanging regions KE2*a* and KE2*b* provided to sandwich the shape changing region KE1 being equal.

In this modification, as for the connection direction CD2 of the second shape unchanging region KE2*b*, the bending angle is turned by angle θ in a plane as shown in FIG. 14 during the period from when the j-th timing signal Tj until the k-th timing signal Tk is generated. As for the connecting portion coordinates C2, too, the bending angle is changed by angle θ in the same plane. Furthermore, it is understood that the insertion section 7 is not twisted or the like.

It is thus possible to calculate a type, a direction and an amount of shape change of the insertion section 7 in the shape changing region KE1 in this modification. In other words, as shown in FIG. 14, the type of change is a bending change and the amount of change is a change in angle θ. The direction of shape change is a clockwise direction as shown in FIG. 14.

The change deriving circuit 32 outputs the type of change, the amount of change and the direction of change of the insertion section 7 to the future shape estimator 33 and the manipulation estimator 34 as the shape change information KA of information of the bending, angle θ and clockwise direction.

The subsequent operation of the endoscope system 1 is the same as that in the first embodiment.

In extracting the shape changing region KE1 and the first and second shape unchanging regions KE2*a* and KE2*b*, a region whose shape change is considerably smaller than that of a region which represents the greatest change of the insertion section 7 or which clearly determines the shape change of the insertion section 7 from the insertion section shape information F calculated by the shape calculator 30, may be extracted. This region can be regarded as a shape unchanging region equivalent to the first and second shape unchanging regions KE2*a* and KE2*b*.

If the region whose shape change is very small is regarded as a shape unchanging region as described above, it is possible to appropriately calculate information of a type of shape change, a direction of shape change and an amount of shape change only for the region whose shape change is great in the insertion section 7.

The change deriving circuit 32 need not necessarily derive information on the shape change throughout the insertion section 7. The change deriving circuit 32 may derive the shape change information KA only for a target portion, a preregistered portion or the like in an operator's manipulation. The operation of the change deriving circuit 32 can thus be simplified.

Advantageous Effect

As described above, the first modification makes it possible to calculate first and second shape unchanging regions KE2*a* and KE2*b* and shape changing region KE1 by the change deriving circuit 32 and then calculate a type of shape change, a direction of shape change and an amount of shape change of the insertion section 7 from the relative arrangement relationship between the shape changing region KE1 and the first and second shape unchanging regions KE2*a* and KE2*b*. More specifically, when the j-th timing signal Tj and the k-th timing signal Tk are generated, it is possible to calculate information of the coordinates of the first and second connecting portions C1 and C2 between the first and second shape unchanging regions KE2*a* and KE2*b* and the shape changing region KE1 and vectors CD1 and CD2 in the tangential direction of the insertion section 7 in these coordinates.

Therefore, like in the foregoing first embodiment, when an operator continues the current manipulation, a shape of the insertion section 7 that may be changed at the next timing can be estimated in advance (a future shape can be estimated). The shape of the insertion section 7 can be displayed to the operator on the display 6 or the like as support information to insert the insertion section 7. Consequently, it is possible to make time required for operator's training and skill improvement shorter than in the conventional endoscope system. Even an inexperienced or low skill level operator can insert and remove the insertion section 7 into and from the internal space 3 of the observation target object 2 relatively easily.

In the first modification, the shape change information KA can be calculated by mathematically treatable parameters of the coordinates of the first connecting portion C1, the coordinates of the second connecting portion C2 and the vectors CD1 and CD2, as compared with the foregoing first embodiment. Thus, programs for achieving the change deriving circuit 32 or programs for achieving the whole of the system 1 can be simplified. Since the programs are simplified, they are suitable for high-speed processing.

Second Embodiment

Next, a second embodiment of the present invention will be described with reference to the drawings. In this embodiment, the same sections as those of the first embodiment will not be described, but only different sections will be described.

The second embodiment differs from the first embodiment in the operations of the change deriving circuit 32, the manipulation estimator 34 and the future shape estimator 33.

[Operation of Change Deriving Circuit 32]

In the foregoing first embodiment, charge deriving circuit 32 is directed to an example of a configuration of comparing the j-th insertion section shape information Fj and k-th insertion section shape information Fk calculated by the shape calculator 30 as shown in FIG. 5, extracting the shape changing region KE1 in which the shape of the insertion section 7 is changed and the first and second shape unchanging regions KE2a and KE2b in which the shape of the insertion section 7 is not changed, and calculates a type of shape change, a direction of shape change and an amount of shape change of the shape changing region KE1 based on the regions KE1, KE2a and KE2b.

In contrast to the above, the second embodiment differs from the first embodiment in the configuration that the change deriving circuit 32 compares the j-th insertion section shape information Fj and the k-th insertion section shape information Fk to extract a similar shape region and calculates a type of shape change, a direction of shape change and an amount of shape change of the insertion section 7 based on the similar shape region.

Figure 15:
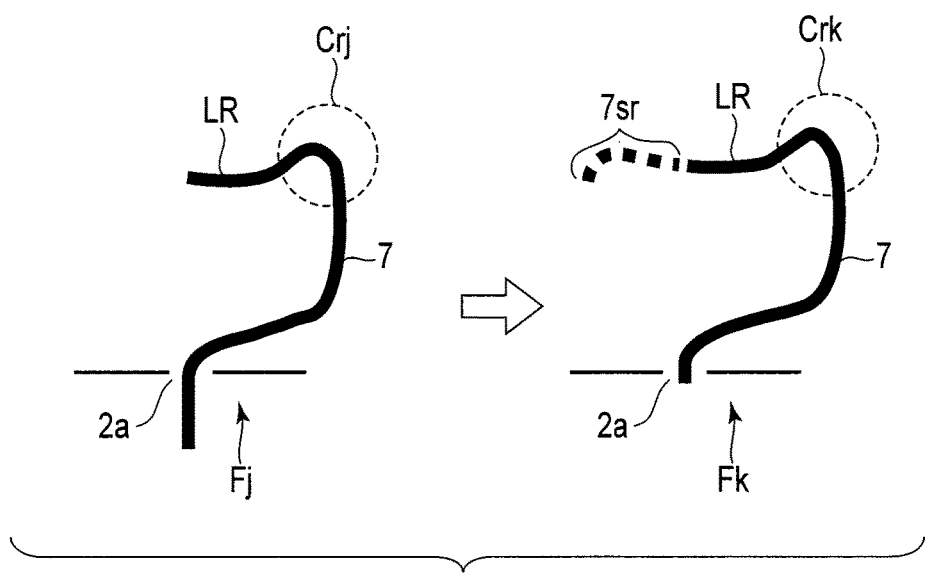
FIG. 15 is an illustration of the j-th and k-th information of insertion section shape upon detection corresponding to the j-th and k-th timing signals.

FIG. 15 shows the j-th insertion section shape information Fj and the k-th insertion section shape information Fk. The j-th insertion section shape information Fj and k-th insertion section shape information Fk include similar shape regions LR whose shapes are similar to each other. A portion including the distal-end portion 7a of the insertion section 7 by the k-th insertion section shape information Fk includes an insertion section moving region 7sr. The insertion section moving region 7sr is a portion in which the insertion section 7 moves during the period from when the j-th timing signal Tj is generated until when the k-th timing signal Tk is generated.

In other words, upon receipt of an operator's manipulation, the insertion section 7 moves in the internal space 3 of the observation target object 2 by the insertion section moving region 7sr during the period from when the j-th timing signal Tj is generated until when the k-th timing signal Tk is generated. During this period, the shape of the similar shape region LR of the insertion section 7 does not change as shown in FIG. 15.

The reason why the shape of the similar shape region LR does not change is as follows. When an operator performs an insertion manipulation, the insertion section 7 moves into the internal space 3 of the observation target object 2 while its shape conforms to the inner surface of the internal space 3 of the observation target object 2. As the insertion section 7 moves, the shape of the insertion section 7 conforms to the inside of the internal space 3 of the observation target object 2 even during the period from when the j-th timing signal Tj is generated until when the k-th timing signal Tk is generated. Therefore, the shape of the insertion section 7 does not change in the similar shape region LR when the j-th timing signal T is generated or in the similar shape region LR when the k-th timing signal T is generated.

It is a point to be noted here that the position of the insertion section 7 corresponding to each position of the similar shape region LR is changed in the j-th insertion section shape information Fj and the k-th insertion section shape information Fk. In other words, the insertion section 7 is moved by its insertion in the j-th insertion section shape information Fj and the k-th insertion section shape information Fk; thus, the detection signals output from the bending shape detectors 8b at the detection points of the shape sensor 8 are different from one another, but there are similar shape regions LR whose shapes are substantially equal to each other in the j-th insertion section shape information Fj and k-th insertion section shape information Fk calculated by the shape calculator 30.

The change deriving circuit 32 compares the j-th insertion section shape information Fj and the k-th insertion section shape information Fk. As a result of the comparison, the change deriving circuit 32 distinguishes the similar shape regions LR whose shapes are substantially equal to each other and the regions other than the similar shape regions LR and extracts the similar shape regions LR.

Figure 16:
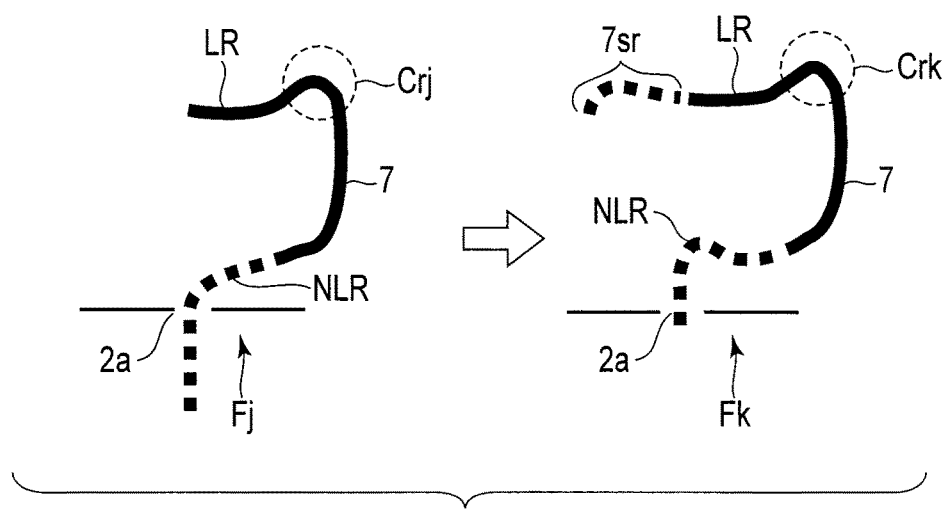
FIG. 16 is an illustration of three regions of an insertion section shape dissimilar region NLR, an insertion section moving region 7$sr$ and an insertion section retreating region.

Each of the regions other than the similar shape regions LR includes three regions of an insertion section shape dissimilar region NLR, an insertion section moving region 7sr and an insertion section retreating region (not shown), for example, as shown in FIG. 16. The insertion section retreating region will be described later.

The insertion section shape dissimilar region NLR is a region that simply differs in shape clearly from the others. The insertion section moving region 7sr is, for example, a region which is not present when the j-th timing signal Tj is generated but newly appears when the k-th timing signal Tk is generated.

The insertion section retreating region is, for example, a region which is present when the j-th timing signal Tj is generated and disappears when the k-th timing signal Tk is generated. In other words, contrary to the insertion section moving region 7sr, it is, for example, the insertion section shape similar region LR a portion of which is lost by a retreat of the insertion section 7.

In the example shown in FIG. 15, the change deriving circuit 32 calculates the insertion section similar shape regions LR whose shapes are substantially equal to each other and the insertion section moving region 7sr appearing when the k-th timing signal Tk is generated. In other words, upon receipt of an operator's manipulation, the insertion section 7 moves in the internal space 3 of the observation target object 2 by the insertion section moving region 7sr. In spite of the movement of the insertion section 7, the portion of the insertion section 7 close to the control section 9 takes substantially the same shape.

It can be estimated that the reason for the above is that the insertion section 7 moves after the shape of the internal space 3 of the observation target object 2. In other words, it can be estimated that even though the insertion section 7 moves in the internal space 3 of the observation target object 2, the regions maintaining the same shape are in the same position relative to the observation target object 2, or they become insertion section similar shape regions LR.

Therefore, in the example shown in FIG. 15, the change deriving circuit 32 estimates that the moving direction of the insertion section 7 is an insertion direction toward the internal space 3 of the observation target object 2 and the moving amount of the insertion section 7 is substantially equal to the length of the insertion section moving region 7sr.

The change deriving circuit 32 sends the moving direction of the insertion section 7 and the amount substantially equal to the length of the insertion section moving region 7sr to the future shape estimator 33 and the manipulation estimator 34 as the shape change information KA.

The shape sensor circuit 23 used in this embodiment is configured to detect a bending direction of the insertion section 7. It is thus possible to determine the bending directions of, e.g. X and Y directions as one of the manipulation states of the insertion section 7 from detection signals D output from the shape sensor circuit 23 when the j-th and k-th timing signals Tj and Tk are generated. For example, if it is determined that there is no change in the X and Y directions from the detection signals D output from the shape sensor circuit 23, the change deriving circuit 32 outputs shape change information KA indicating that there is no change in the shape of the insertion section 7. Upon receiving the shape change information KA indicating that there is no change in the shape of the insertion section 7, the manipulation estimator 34 estimates that the insertion section 7 is simply inserted.

If there is a change in the X and Y directions from the detection signals D, the change deriving circuit 32 outputs shape change information KA indicating that there is a change in the X and Y directions in the shape of the insertion section 7. Upon receiving the shape change information KA indicating that there is a change in the shape of the insertion section 7, the manipulation estimator 34 estimates that for example, the insertion section 7 is manipulated in the twist direction, too based on the change in the shape of the insertion section 7 in the X and Y directions.

There is a case where an insertion section moving region 7sr, an insertion section retreating region (not shown) or an insertion section shape dissimilar region NLR is not present in the insertion section close to the distal end of the insertion section similar shape region RL. This case indicates that the distal end of the insertion section 7 is stopped.

There is a case where an insertion section dissimilar shape region NLR is present in the insertion section 7 closer to the control section 9 than the insertion section similar shape region LR. The insertion section dissimilar shape region NLR is caused by an operator's manipulation.

FIG. 16 shows an example where when an operator's manipulation is performed, the distal-end portion of the insertion section 7 is moved by the length of the insertion section moving region 7sr, and further an insertion section shape similar region LR is generated in the insertion section 7 close to the control section 9. Thus, the direction of the operator's manipulation corresponds to the insertion direction of the insertion section 7. The amount of manipulation is substantially equal to the sum of the length of the insertion section moving region 7sr and the length corresponding to the insertion amount required to cause the insertion section dissimilar shape region NLR.

[Operation of Manipulation Estimator 34]

The manipulation estimator 34 estimates an operator's manipulation and outputs it as the operator manipulation information L. Assuming that the shape change of the insertion section 7 is a result of the operator's manipulation, the manipulation estimator 34 estimates a manipulation performed during the period from when the j-th timing signal Tj is generated until when the k-th timing signal Tk is generated on the basis of the shape change information KA, and outputs it as the operator manipulation information L.

In this embodiment, the estimation of the operator's manipulation has been described for only the operator's direct manipulation, but the manipulation estimator 34 can estimate the manipulation performed by the control handle 11.

Comparing the j-th insertion section shape information Fj with the k-th insertion section shape information Fk, almost all of the insertion sections 7 become the insertion section similar shape region LR in the observation target object 2 from the insertion opening 2a to the internal space 3 as shown in FIG. 15. In the k-th insertion section shape information Fk, when an operator's manipulation is performed, the insertion section 7 moves into the internal space 3 of the observation target object 2 by the length of the insertion section moving region 7sr.

Therefore, the manipulation estimator 34 estimates that the operator performs a push operation in the insertion direction to move the insertion section 7 into the internal space 3 of the observation target object 2 by the length of the insertion section moving region 7sr.

The manipulation estimator 34 estimates that the type of the manipulation is a push and the direction of the manipulation is the central axis direction of the insertion section 7 exposed from the insertion opening 2a. It estimates that the insertion amount of the insertion section 7 is the length of the insertion section moving region 7sr.

The length of the insertion section moving region 7sr can be estimated based on characteristic portions Crj and Crk of the insertion section 7 as shown in, e.g. FIGS. 15 and 16. The characteristic portions Crj and Crk of the insertion section 7 can be estimated by the positions of the bending shape detectors 8b provided in the optical fiber sensor 8 of the shape sensor circuit 23 on the insertion section 7, information from the calculation circuit of insertion section shape upon detection 30, information of the change deriving circuit 32, and the like. The characteristic portions Crj and Crk in this embodiment are each set in such a manner that the insertion section 7 is bent to take a specific shape such as a shape portion include a convex portion that is more acute than the other portion and a shape portion whose shape is not smooth like the convex portion. The characteristic portion Crj is a shape portion that appears when the j-th timing signal T is generated, and the characteristic portion Crk is a shape portion that appears when the k-th timing signal T is generated.

If a bending shape detector 8b that is located, e.g. 20 cm from the distal-end portion 7a of the insertion section 7 is exactly aligned with the top of the characteristic portion Crj when the j-th timing signal Tj is generated, it is understood that the characteristic portion Crj is located 20 cm from the distal end of the insertion section 7.

If the intermediate location between another bending shape detector 8b that is located, e.g. 30 cm from the distal-end portion 7a of the insertion section 7 and another bending shape detector 8b that is located, e.g. 40 cm from the distal-end portion 7a is exactly aligned with the top of the characteristic portion Crk when the k-th insertion section shape information Fk is generated, it is understood that the characteristic portion Crk is located 35 cm from the distal end of the insertion section 7.

Thus, the amount of insertion of the insertion section 7 into the internal space 3 of the observation target object 2, namely the length of the insertion section moving region GR is a difference between the position (35 cm) of the characteristic portion Crk at the time of generation of the k-th timing signal Tk and the position (20 cm) of the characteristic portion Crj at the time of generation of the j-th timing signal Tj: 35 cm−20 cm=15 cm.

As shown in FIG. 16, when the insertion section 7 includes the dissimilar shaped region NLR, the insertion amount of the insertion section 7 needs to be set in consideration of a change in the length of the dissimilar shaped region NLR in the insertion section 7. In this case, since the dissimilar shape region NLR is in the insertion section 7 close to the control section 9, the length of the insertion section moving region GR cannot be calculated using the positions of the characteristic portions Crj and Crk.

In the above case, the manipulation estimator 34 can calculate the length of the insertion section 7 from the detection signal D output from the shape sensor circuit 23. In other words, the shape sensor circuit 23 can detect the shape information of the insertion section 7 as relative position information and thus the length of the insertion section 7 can be obtained by a variety of mathematical techniques.

Assuming that the difference between the length of the dissimilar shape region NLR of the insertion section 7 at the time of generation of the j-th timing signal Tj and that of the dissimilar shape region NLR of the insertion section 7 at the time of generation of the k-th timing signal Tk is, for example, 5 cm as shown in FIG. 16, the manipulation estimator 34 calculates the insertion amount of the insertion section 7 as 20 cm that is the length obtained by adding 5 cm to 15 cm that has previously been obtained. The insertion amount of 20 cm is sent to the future shape estimator 33 as operator manipulation information L.

Needless to say, FIG. 15 shows an example of obtaining the insertion amount of the insertion section 7 using characteristic portions Crj and Crk, but the difference in length of the insertion section 7 calculated based on information detected by the shape sensor circuit 23 can be calculated as the insertion amount of the insertion section 7.

[Operation of Future Shape Estimator 33]

The future shape estimator 33 receives either or both of the shape change information KA output from the change deriving circuit 32 and the operator manipulation information L output from the manipulation estimator 34 to estimate a future shape of the insertion section 7 based on either or both of the shape change information KA and the operator manipulation information L.

In this embodiment, an example using the operator manipulation information L will be described with reference to FIG. 15.

As described above, the manipulation type is a push, the manipulation direction is the central axis of the insertion section 7 exposed from the insertion opening 2a to the outside, and the manipulation amount is the length of the insertion section moving region 7sr, for example, 15 cm.

The future shape estimator 33 estimates insertion section future shape information M based on the push that is the manipulation type, the direction of the central axis of the insertion section 7 that is the manipulation direction, and the length of the insertion section moving region 7sr that is the manipulation amount.

Assume that h is a natural number that is larger than k.

Though the shape sensor controller 31 has already output the j-th and k-th timing signals Tj and Tk, it has not yet output the h-th timing signal Th but is in a state of readiness to output it in the future. Assume here that the time interval between the j-th and k-th timing signals Tj and Tk is equal to the time interval between the k-th and h-th timing signals Tk and Th. The timing signal T is represented as an image output as time elapses as shown in FIG. 9.

The future shape estimator 33 estimates insertion section future shape information M after a push manipulation is performed by, e.g. 15 cm toward the central axis direction of the insertion section 7 exposed from the insertion opening 2a and further on the assumption that same manipulation is performed by the same manipulation amount in the same direction.

When an operator's manipulation is performed during the period from the generation of the j-th timing signal Tj until the generation of the k-th timing signal Tk as shown in FIG. 15, the insertion section 7 is inserted into the internal space 3 of the observation target object 2.

Therefore, the future shape estimator 33 estimates the insertion section future shape information M of the insertion section 7 as the insertion section 7 pushed by another 15 cm, as in the above manipulation.

At that time, in this embodiment, it is predicted that the distal-end portion 7a of the insertion section 7 moves to a region of the internal space 3 of the observation target object 2, which the distal-end portion 7a has not yet reached. It is thus necessary to estimate information of the region, or information of the more distal end side of the insertion section moving region 7sr as shown in FIG. 15.

FIG. 17A shows the j-th insertion section shape information Fj and FIG. 17B shows the k-th insertion section shape information Fk. The k-th insertion section shape information Fk includes the estimated insertion section moving region 7sr.

Figure 17C:
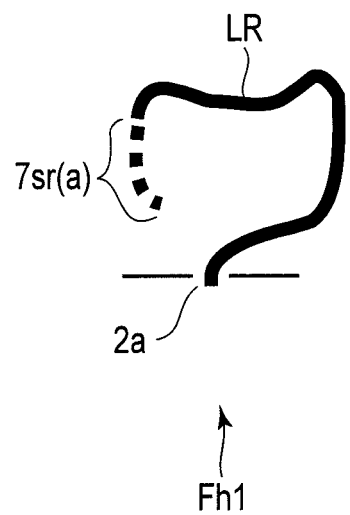
FIG. 17C is an illustration of the h-th insertion section shape information Fh1 upon detection in the case where approximate information such as the shape of an internal space of an observation target object is obtained.

FIG. 17C shows insertion section shape information Fh1 output from the shape calculator 30 when the h-th timing signal Th is generated in the case where approximate information such as the shape of the internal space 3 of the observation target object 2 is obtained. The insertion section shape information Fh1 includes the estimated insertion section moving region 7sr(a). In other words, the future shape estimator 33 estimates future shape estimation information M as the insertion section 7 moving such that the insertion section moving region 7sr(a) is based on approximate shape information of the internal space 3 of the observation target object 2.

On the other hand, when no approximate information such as the shape of the internal space 3 of the observation target object 2 is obtained, the future shape estimator 33 assumes the shape of the insertion section, e.g. a preset shape such as a linear shape as a temporary shape and estimates the insertion section future shape information M of the insertion section 7 based on information of the temporary shape.

Figure 17D:
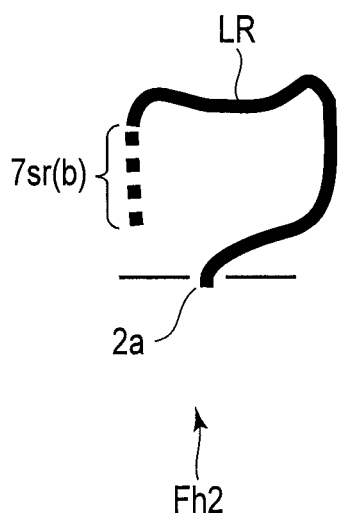
FIG. 17D is an illustration of the h-th insertion section shape information Fh2 upon detection in the case where approximate information such as the shape of the internal space of the observation target object is not obtained.

FIG. 17D shows insertion section shape information Fh2 output from the shape calculator 30 when the h-th timing signal T is generated in the case where approximate information such as the shape of the internal space 3 of the observation target object 2 is not obtained. The insertion section shape information Fh2 includes the estimated insertion section moving region 7sr(b). As compared with the foregoing insertion section moving region 7sr(a), the insertion section moving region 7sr(b) is shaped linearly.

The future shape estimator 33 estimates a future shape of the insertion section 7 on the assumption that the insertion section 7 moves further by the amount of an operator's manipulation with the shape the similar shape region LR of the insertion section 7 unchanged.

As described above, according to the second embodiment, the change deriving circuit 32 compares the shape information items of the insertion section 7 at different timings to extract a similar shape region LR and calculate a type of the shape change of the insertion section 7, a direction of the shape change and an amount of the shape change on the basis of the similar shape region LR. The manipulation estimator 34 estimates that the insertion section 7 moves into the internal space 3 of the observation target object 2 by the length of the insertion section moving region 7sr when an operator performs a push operation. The future shape estimator 33 estimates insertion section future shape information M on the basis of the push that is a type of manipulation, the central axis direction of the insertion section 7 that is a direction of the manipulation, and the length of the insertion section moving region 7sr that is an amount of the manipulation.

Thus, when the operator continues the current manipulation, a future shape of the insertion section 7 that may be taken at the next timing can be estimated, and the estimated shape can be displayed to the operator on the display 6 or the like as the insertion manipulation support information and thus provided for the operator.

Consequently, it is possible to make time required for training and skill improvement shorter than in the conventional endoscope system. Even an inexperienced or low skill level operator can insert and remove the insertion section 7 into and from the internal space 3 of the observation target object 2 relatively easily.

In this embodiment in particular, even though the overall shape of the insertion section 7 is changed, a future shape of the insertion section 7 that may be taken at the next timing can be estimated because a similar shape region LR that is similar to the shape of the insertion section 7 is detected.

[First Modification to Second Embodiment]

Next, a first modification to the second embodiment will be described with reference to the drawings. In this modification, the same sections as those of the second embodiment will not be described, but only different components will be described.

This modification differs from the second embodiment in the operation of the change deriving circuit 32. The foregoing second embodiment is directed to an example of calculating a moving direction and a moving amount of the insertion section 7 as shape change information KA using an insertion section similar shape region LR. In this first modification, the insertion section similar shape region LR is replaced with a top distance same region that is a spacing between the tops of the bending portions of the insertion section 7.

[Operation of Change Deriving Circuit 32]

Figure 18:
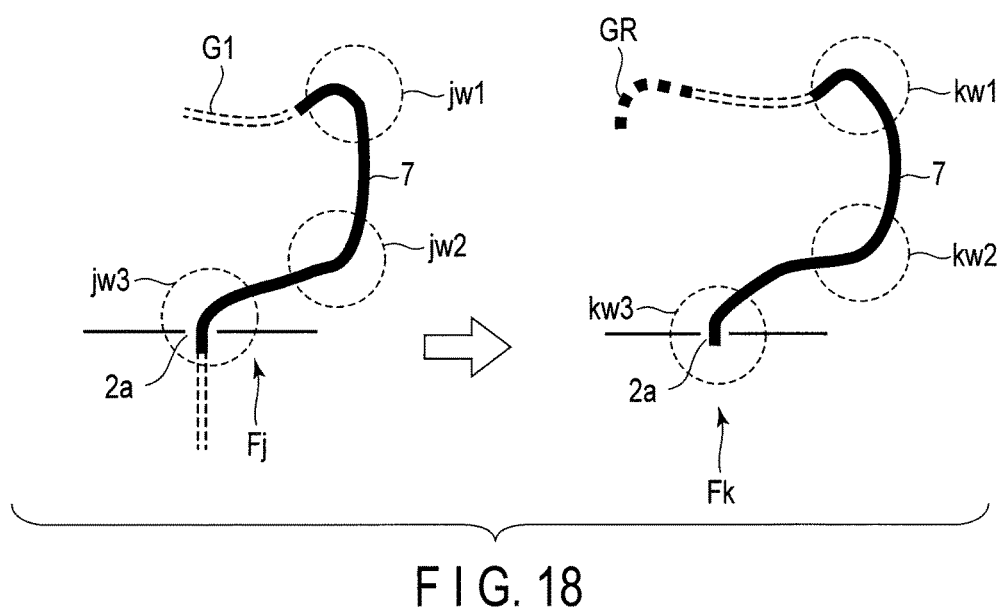
FIG. 18 is an illustration of an example of the first to third characteristic portions in the j-th and k-th insertion section shape information Fj and Fk upon detection in a first modification to the second embodiment of the present invention.

FIG. 18 illustrates an example of the j-th and k-th insertion section shape information Fj and Fk. Unlike in the foregoing first embodiment, in this modification, the shape of the insertion section 7 cannot be classified into the first and second shape unchanging regions KE2a and KE2b and the shape changing region KE1, and unlike in the foregoing second embodiment, in this modification, an insertion section similar shape region LR cannot be extracted. On the other hand, if there are a plurality of bending portions and the distances between the tops of these bending portions are equal to each other, this modification can be applied.

For example, the j-th and k-th insertion section shape information Fj and Fk each include three bending portions. These bending portions are referred to as first, second and third characteristic portions jw1, jw2 and jw3 in the j-th insertion section shape information Fj and referred to as first, second and third characteristic portions kw1, kw2 and kw3 in the k-th insertion section shape information Fk.

The first characteristic portion jw1, the second characteristic portion jw2, ..., the third characteristic portion kw3 each have a top of the corresponding bending portion.

The spacings between the tops of the first to third characteristic portions jw1 to jw3 and the first to third characteristic portions kw1 to kw3 in the j-th insertion section shape information Fj and the like are equal, as are the bending directions. The fact that the spacings between the tops and the bending directions are equal in the first to third characteristic portions jw1 to jw3 and the first to third characteristic portions kw1 to kw3, is recognized by comparing the positions of the first to third characteristic portions jw1 to jw3 and those of the first to third characteristic portions kw1 to kw3. G1 FIG. 18 represents a region not sandwiched between the first to third characteristic portions. There are a plurality of regions G1, but FIG. 18 shows one region G1 as an example because all the regions are difficult to show therein.

First, the change deriving circuit 32 calculates the coordinates of the top of each of the bending portions in the insertion section 7. The coordinates of the top of each of the bending portions can be obtained easily from the j-th and k-th insertion section shape information Fj and Fk.

The change deriving circuit 32 calculates the distance between the tops of the bending portions in the insertion section 7 and the bending directions thereof from the coordinates of the tops of the bending portions. The bending directions are relative to the tops of the bending portions.

In other words, in the j-th insertion section shape information Fj, a relative positional relationship and spacings between the first, second and third characteristic portions jw1, jw2 and jw3 are obtained. Similarly, in the k-th insertion section shape information Fk, a relative positional relationship and spacings between the first, second and third characteristic portions kw1, kw2 and kw3 are obtained.

The relative positional relationship and spacings between the first, second and third characteristic portions jw1, jw2 and jw3 in the j-th insertion section shape information Fj and the relative positional relationship and spacings between the first, second and third characteristic portions kw1, kw2 and kw3 in the k-th insertion section shape information Fk can be calculated with their coordinates information on a common coordinate axis.

The spacings between the tops of the first, second and third characteristic portions jw1, jw2 and jw3 and the spacings between the tops of the first, second and third characteristic portions kw1, kw2 and kw3 can be obtained as information of scalar quantity and including direction information of the bending direction as vectors.

To obtain the positional relationship and spacings, the first to third characteristic portions jw1 to jw3 and the first to third characteristic portions kw1 to kw3 can be compared by any technique and method.

The change deriving circuit 32 compares a relative positional relationship and spacings between the first, second and third characteristic portions jw1, jw2 and jw3 in the j-th insertion section shape information Fj and a relative positional relationship and spacings between the first, second and third characteristic portions kw1, kw2 and kw3 in the k-th insertion section shape information Fk to extract substantially the same positional relationship and spacings as the first, second and third characteristic portions jw1, jw2 and jw3 in the j-th insertion section shape information Fj and as the first, second and third characteristic portions kw1, kw2 and kw3 in the k-th insertion section shape information Fk.

The tops of the first, second and third characteristic portions jw1, jw2 and jw3 and those of the first, second and third characteristic portions kw1, kw2 and kw3 must be present on a straight line if there is nothing around the tops. However, it is very likely that the insertion section 7 will be bent by the structure of the internal space 3 of the observation target object 2 when it is inserted into the internal space 3 of the observation target object 2.

It is also very likely that the convex side of the insertion section 7 will be brought into contact with the internal space 3 of the observation target object 2 because the tops of the first characteristic portion jw1, the second characteristic portion jw2, . . . , the third characteristic portion kw3 in the j-th and k-th insertion section shape information Fj and Fk are convex.

Furthermore, in the internal space 3 of the observation target object 2, a portion that is bent by the characteristics of the tube hole-like shape of the internal space 3 and brought into easy contact with the insertion section 7 is determined to some extent. For this reason, when the relative positional relationship and spacings between the tops of the first characteristic portion jw1, the second characteristic portion jw2, . . . , the third characteristic portion kw3 in the j-th and k-th insertion section shape information Fj and Fk are substantially equal, the insertion section 7 is very likely to be in contact with the same inner wall surface of the internal space 3 of the observation target object 2. In other words, it can be estimated that the insertion section 7 exists in the same location.

When the relative positional relationship between the first to third characteristic portions jw1 to jw3 in the j-th insertion section shape information Fj and the relative positional relationship between the first to third characteristic portions kw1 to kw3 in the k-th insertion section shape information Fk are substantially equal to each other, the change deriving circuit 32 determines that the first characteristic portions jw1 and kw1 are present in the same position, the second characteristic portions jw2 and kw2 are present at the same position and the third characteristic portions jw3 and kw3 are present in the same position.

Furthermore, the change deriving circuit 32 obtains a moving direction and a moving amount of the insertion section 7 based on information about the spacings between the tops of the first to third characteristic portions jw1 to jw3 and the tops of the first to third characteristic portions kw1 to kw3 and the bending directions thereof. As for the moving direction, it is understood that if the j-th insertion section shape information Fj and the k-th insertion section shape information Fk are compared, the insertion section 7 moves into the internal space 3 of the observation target object 2 by the length of the insertion section moving region GR as shown in FIG. 18. The moving direction is therefore the insertion direction of the insertion section 7. The moving amount of the insertion section 7 corresponds to a length obtained by adding the difference in lengths between the first to third characteristic portions to a length that is substantially equal to the insertion section progression region GR. The moving amount of the insertion section 7 can be obtained in the same manner as the moving amount of the insertion section 7 in the foregoing second embodiment. Moreover, future shape information M can be estimated using the same technique as that of estimating a future shape of the insertion section 7 in the foregoing second embodiment. Thus, when the operator continues the current manipulation, a future shape of the insertion section 7 that may be taken at the next timing can be estimated, and the estimated shape can be displayed to the operator on the display 6 or the like as the insertion manipulation support information and thus provided for the operator.

Consequently, it is possible to make time required for operator's training and skill improvement shorter than in the conventional endoscope system. Even an inexperienced or low skill level operator can insert and remove the insertion section 7 into and from the internal space 3 of the observation target object 2 relatively easily.

Third Embodiment

A third embodiment of the present invention will be described below with reference to the drawings. The same sections as those of the first and second embodiments are denoted by the same sign and their detailed descriptions will be omitted.

The this embodiment differs from the first and second embodiments in including an inner profile information estimation circuit (referred to as a profile estimator hereinafter) 50 which estimates at least part of the inner profile of the internal space 3 of the observation target object 2.

The inner profile represents the shape information of the inner surface of the internal space 3 of the observation target object 2. In the insertion/removal system chiefly including an endoscope, the observation target object 2 may often include a narrow internal space 3. The insertion section 7 moves in the depth direction of the internal space 3 of the observation target object 2 along the shape of the narrow internal space 3 to perform the operation.

For this reason, part of the insertion section 7 of the insertion/removal system is moved in the depth direction by an operator's manipulation while contacting the inner surface of the internal space 3 of the observation target object 2. If, therefore, it can be estimated that the insertion section 7 is in contact with the inner surface of the observation target object 2, the inner profile of the observation target object 2 can roughly be estimated. If the inner profile of the observation target object 2 can be estimated, it can be used to estimate a future shape of the insertion section 7. Inner profile information can thus be provided for the operator, and the insertion/removal system can be achieved more easily.

Figure 19:
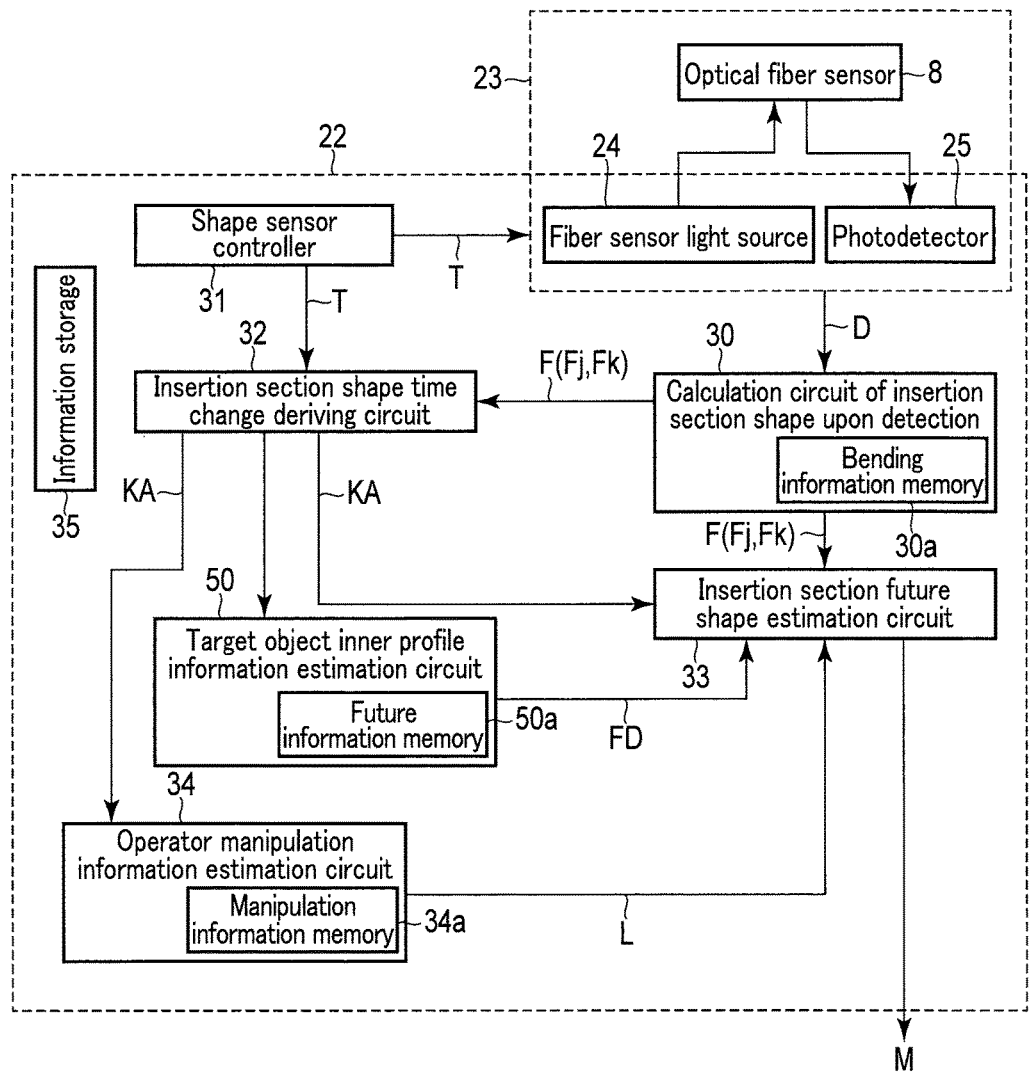
FIG. 19 is a configuration diagram showing a support information circuit in a third embodiment of the present invention.

FIG. 19 is a configuration diagram showing a support information circuit 22. The basic configuration of the support information circuit 22 is the same as that in the above first embodiment. The support information circuit 22 in this embodiment includes a profile estimator 50 for the observation target object 2. In other words, the support information circuit 22 includes a profile estimator 50 for the observation target object 2 in addition to the shape calculator 30, shape sensor controller 31, change deriving circuit 32, future shape estimator 33 and manipulation estimator 34.

Upon receipt of information from the change deriving circuit 32, the profile estimator 50 estimates inner profile information FD of the observation target object 2 and sends it to the future shape estimator 33. The inner profile information FD can also be provided for an operator via the display 6 as support information.

Next is a description of the operation of the support information circuit 22 configured as described above.

The basic operation of the support information circuit 22 is the same as those in the above-described first and second embodiments, and different operations will be described.

The profile estimator 50 estimates the inner profile of the observation target object 2 based on information from the change deriving circuit 32. The profile estimator 50 includes a future profile information memory 50a. The future profile information memory 50a stores prior information about the inner profile of the observation target object 2 in advance.

The profile estimator 50 estimates the inner profile of the observation target object 2 using prior information about the inner profile of the observation target object 2 which is stored in advance in the future profile information memory 50a.

[Operation of Profile Estimator 50]

The profile estimator 50 estimates the inner profile of the observation target object 2 like the following first to fifth functions with respect to the information from the change deriving circuit 32.

(First Function)

There is a case where though the overall shape of the insertion section 7 varies with time, the insertion section 7 includes regions of partly the same shape. In this case, it is estimated that the regions of the same shape in the insertion section 7 take a shape approximate to the inner profile on the assumption that the regions take a shape after the inner shape of the internal space 3 of the observation target object 2.

(Second Function)

When the positional relationship of the characteristic portions, for example, the relative positional relationship between the first to third characteristic portions jw1 to jw3 in the j-th insertion section shape information Fj and the relative positional relationship between the first to third characteristic portions kw1 to kw3 in the k-th insertion section shape information Fk are equal to each other, it is estimated that the insertion section 7 is in the same position in the internal space 3 of the observation target object 2 and, for example, the tops (outside) of the characteristic portions are in contact with the inner surface of the internal space 3 of the observation target object 2.

(Third Function)

As in the above second function, when the positional relationships of the characteristic portions are equal and when the regions between the characteristic portions are convex, it is estimated that the regions are also in contact with the inner surface of the internal space 3 of the observation target object 2.

(Fourth Function)

When a plurality of discrete inner profile regions can be connected smoothly, the inner profile is estimated based thereon.

(Fifth Function)

When a plurality of inner profiles are not connected smoothly, they are estimated in the following order of priority: the first function, the second function, the third function and the fourth function. As for the inner profiles in the low order, it is determined that they cannot be estimated to delete information about the estimation.

Next is a description of the operation of the profile estimator 50. In the description of the operation, an example of estimating an inner profile will be described using the example of the first embodiment shown in FIG. 5 with reference to the examples described in the foregoing first and second embodiments. Assume that as prior information, the observation target object 2 is an organ of a living body. Assume that an organ to be observed can be moved in the living body to some extent by the pushing force of the insertion section 7. Assume that the prior information is stored in the future profile information memory 50a of the profile estimator 50. Assume also that the fact that the organ is a cylindrical organ such as the large intestine is stored in the future profile information memory 50a.

A process of estimating the inner profile by the profile estimator 50 in the above case will be described.

The profile estimator 50 estimates an inner profile around the shape unchanging regions KE2a and KE2b by the first function.

Next, the profile estimator 50 estimates the inner profile of the top (outside) of the bending of the shape changing region KE1 by the third function.

Figure 20:
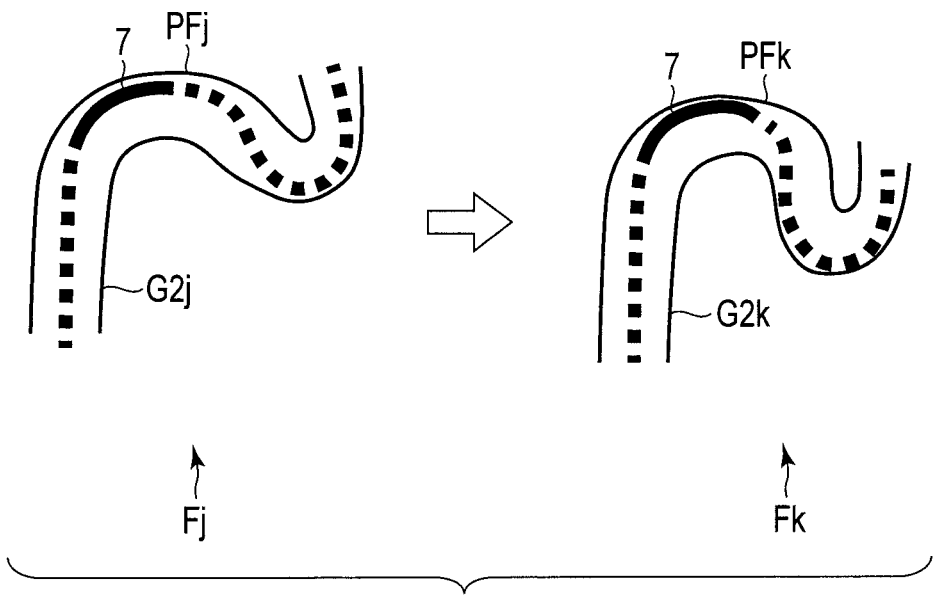
FIG. 20 is an illustration of the inner profiles of the internal space of the observation target object corresponding to the j-th and k-th shape information Fj and Fk.

Finally, the profile estimator 50 estimates the profile of the inside of the top of the bending from the information indicating that the observation target object 2 is cylindrical. In this example, the profile estimator 50 can estimate the inner profile of the entire region including the insertion section 7 as shown in FIG. 20. In the shape unchanging region KE2b on the distal-end side of the insertion section 7, the inner wall of the observation target object 2 moves and accordingly the inner profile varies.

Next, the inner profile estimation process will be described using the example of the second embodiment shown in FIG. 15. In this example, assume that information on the inner profile of the observation target object 2 is not stored in the future profile information memory 50a. In this case, the inner profile of the whole of the insertion section 7 cannot be estimated as shown in FIG. 21.

The profile estimator 50 estimates the inner profile of three convex portions by the second function on the assumption that they are in contact with the inner surface of the observation target object 2.

Along with this, the profile estimator 50 estimates the inner profile of the side of the insertion section similar shape region LR in its convex direction in the insertion section 7 by the third function on the assumption that the insertion section 7 is in contact with the inner surface of the observation target object 2.

Figure 21:
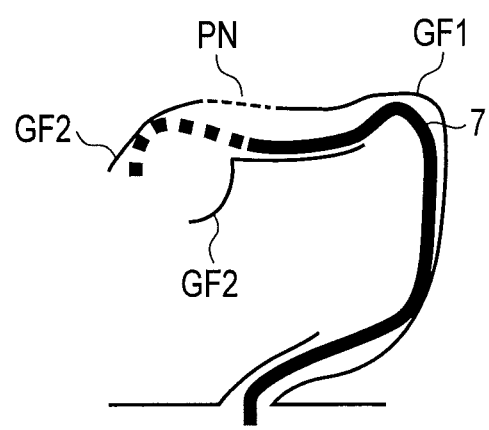
FIG. 21 is an illustration of an operation performed by a target object inner profile information estimation circuit.

Furthermore, the profile estimator 50 uses the fourth function to connect a region (e.g., the inner profile PN indicated by the dotted line in the upper part of FIG. 21) by which discrete portions are likely to be connected smoothly by the first function estimation and the third function estimation and expand a region capable of estimating the inner profile. In this example, the inner profile cannot be estimated throughout the insertion section 7, but information about a portion that cannot be estimated can be provided, displayed and the like by assuming a cylindrical shape. The estimated target object inner profile information FD is stored in the information storage 35. The estimated target object inner profile information FD can also be output to the display 6.

Figure 22:
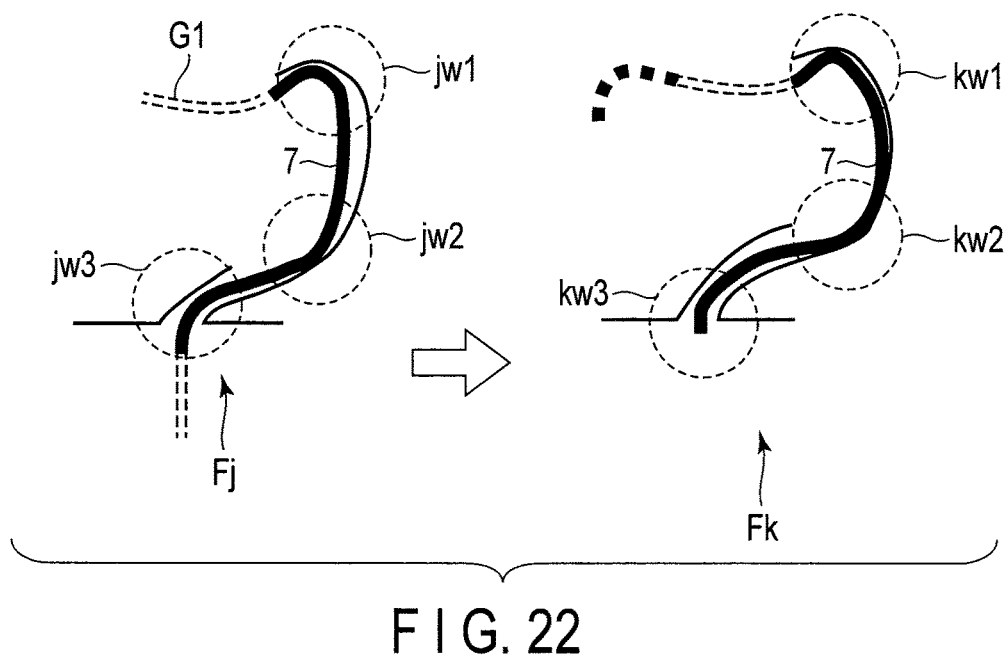
FIG. 22 is an illustration of an operation performed by the target object inner profile information estimation circuit.

The inner profile estimation process will also be described using the example of the second embodiment shown in FIG. 18. In this example, too, assume that information on the inner profile of the observation target object 2 is not stored in the future profile information memory 50a. In this case, the inner profile of the whole insertion section 7 cannot be estimated as in the example shown in FIG. 15, but it can be estimated that the insertion section 7 is in the same region of the observation target object 2 by utilizing the fact that the relative positional relationship between the characteristic portions is substantially equal by the second function. At this time, a region between the first and second characteristic portions jw1 and jw2 and a region between the second and third characteristic portions jw2 and jw3 are slightly projected toward the right side of the figure. This allows the inner profile of these regions to be estimated as shown in FIG. 22 by the third function.

Furthermore, a region between the second and third characteristic portions jw2 and jw3 is projected toward the lower right side of the figure in the j-th insertion section shape information Fj, and a region between the second and third characteristic portions kw2 and kw3 is slightly projected toward the upper left side of the figure in the k-th insertion section shape information Fk. Thus, the upper left side inner profile of these regions cannot be estimated in the j-th insertion section shape information Fj upon detection, but can be estimated by the third function using the k-th insertion section shape information Fk.

A region whose inner profile can be estimated may change to a region whose inner profile cannot be estimated due to a change in shape of the insertion section 7. In this case, the profile estimator 50 determines that the inner profile is present and continues to operate because it is hard to consider that the inner surface of the observation target object 2 appears or disappears.

Furthermore, in this embodiment, the insertion/removal system is an endoscope apparatus. The profile estimator 50 can process an imaging signal output from the image sensor 7d naturally included in the endoscope apparatus to acquire an observation image and estimate inner profile information using the observation image and the like. For example, the profile estimator 50 can know from the observation image whether the inner surface of the observation target object 2 is a broad space or cylindrical. The profile estimator 50 can improve the reliability of the inner profile information by automatic or operator's input based on the information.

The profile estimator 50 can store the inner profile information FD estimated by the foregoing process in the information storage 35 and output it in the future shape estimator 33. The profile estimator 50 can also output it to the display 6.

[Operation of Future Shape Estimator 33]

An operation of the future shape estimator 33 will be described using an example used in the first embodiment shown in FIGS. 5 and 20.

FIG. 20 shows inner profiles G2j and G2k of the internal space 3 of the observation target object 2 corresponding to the j-th and k-th insertion section shape information Fj and Fk.

As described above, the observation target object 2 has a cylindrical inner profile such as a large intestine. Information indicating that the observation target object 2 can be moved inside the living body is stored in the future profile information memory 50a.

As shown in FIG. 20, the inner profiles G2j and G2k of the observation target object 2 are greatly deformed at the distal-end side of the insertion section 7 between the j-th and k-th insertion section shape information Fj and Fk. This deformation of the inner profiles G2j and G2k is due to the pushing force from the insertion section 7. Even though an organ is movable in a living body, the movement of the organ is limited. Thus, when the same pushing force is applied to the insertion section 7, it is predicted that the insertion section 7 is not deformed by the same amount but its deformation amount gradually decreases.

Incidentally, GF1 represents the inner profile estimated by the first function and GF2 represents the inner profile estimated by the third function.

Considering this information, the future shape estimator 33 estimates that the deformation amount is smaller than the insertion section future shape information M at the time of generation of the h-th timing signals Th shown in FIGS. 10, 11 and 12 of the first embodiment.

When information such as a distance by which the inner surface of the observation target object 2 can be moved and stress required for the movement, is stored in the future profile information memory 50a, the future shape estimator 33 performs a suitable, physical arithmetic operation using the information to estimate the insertion section future shape information M. The estimated insertion section future shape information M is stored in the information storage 35.

The foregoing description is directed to an example where the inner profiles G2j and G2k of the observation target object 2 are movable. If the future profile information memory 50a stores the fact that they are immovable like those of industrial pipes, the future shape estimator 33 estimates the insertion section future shape information M by determining that the insertion section 7 is present only in the inner profiles G2j and G2k of the observation target object 2, which are estimated as being immovable.

With the configuration of the third embodiment as described above, when the operator continues the current manipulation, a future shape of the insertion section 7 that may be taken at the next timing can be estimated, and it can be displayed and provided for the operator as insertion manipulation support information. Consequently, this embodiment brings about the advantages that time required for operator's training and skill improvement is made shorter than in the conventional endoscope system and even an inexperienced or low skill level operator can insert and remove the endoscope relatively easily.

If the inner profiles G2j and G2k of the observation target object 2 can be estimated as in this embodiment in particular, information of, e.g. the configuration of the internal space 3 of the observation target object 2 and the positional relationship between the observation target object 2 and the insertion section 7 can be provided, thus producing the advantage that the operator easily grasps information at different times intuitively.

[First Modification to Third Embodiment]

Next is a description of a first modification to the third embodiment.

Figure 23:
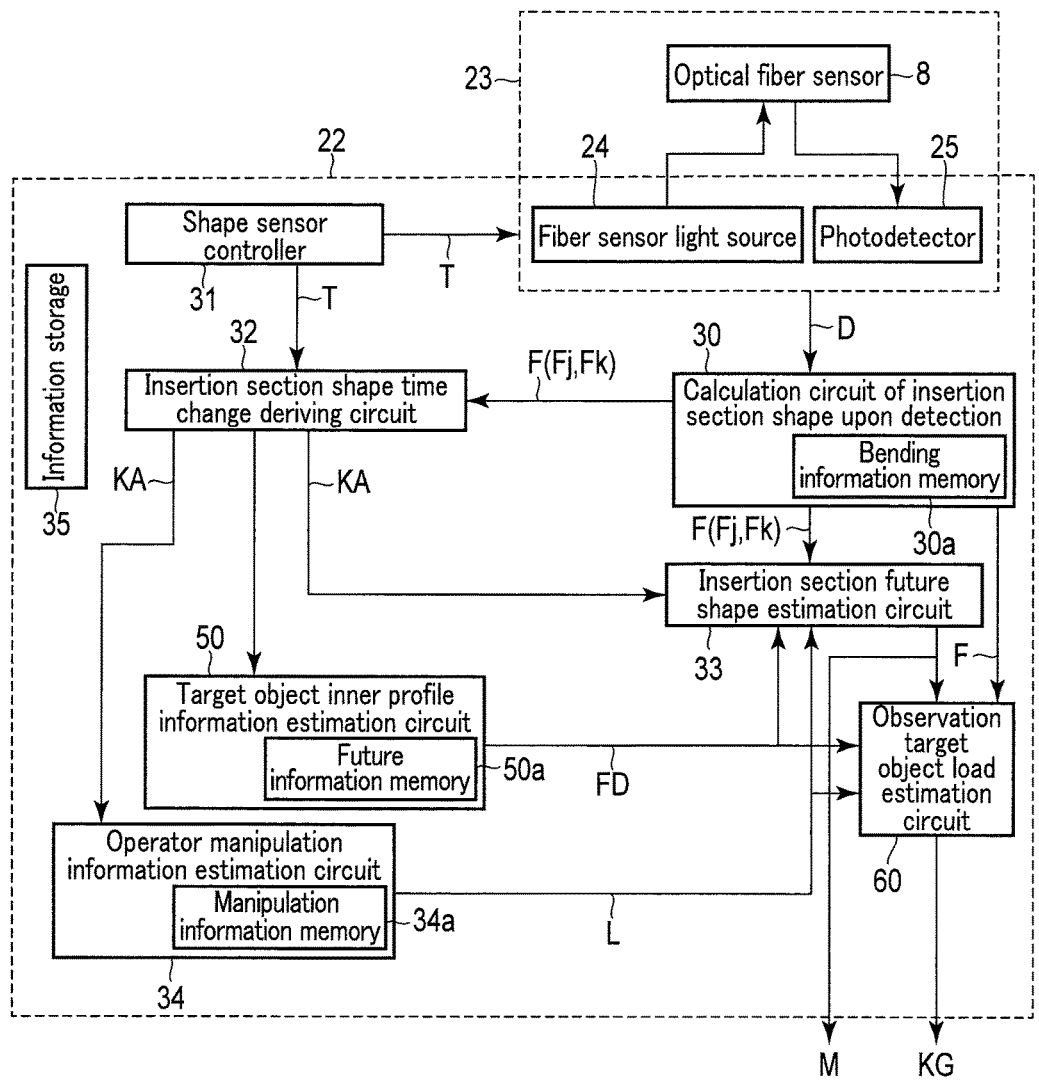
FIG. 23 is a configuration diagram showing a support information circuit in a first modification to the third embodiment of the present invention.

FIG. 23 is a configuration diagram showing a support information circuit 22 of the present modification. The foregoing embodiment is directed to an example including the profile estimator 50. The support information circuit 22 in this modification includes an observation target object load estimation circuit (referred to as a load estimator hereinafter) 60 which estimates load estimation information of the observation target object 2 as shown in FIG. 23. In this respect, the present modification differs from the third embodiment.

The load estimator 60 combines the inner profile information FD from the profile estimator 50, the insertion section shape information F from the insertion section shape estimation circuit upon detection 30, the operator manipulation information L from the manipulation estimator 34, and/or the insertion section future shape information M from the future shape estimator 33 to estimate a load applied to the observation target object 2 as the observation target object load estimation information KG.

An example of combining the inner profile information FD and the insertion section shape information F will be described. In this example, it is assumed that the observation target object 2 is sufficiently stiff relative to the insertion section 7 and the inner profile of the observation target object 2 will not be deformed.

Figure 24:
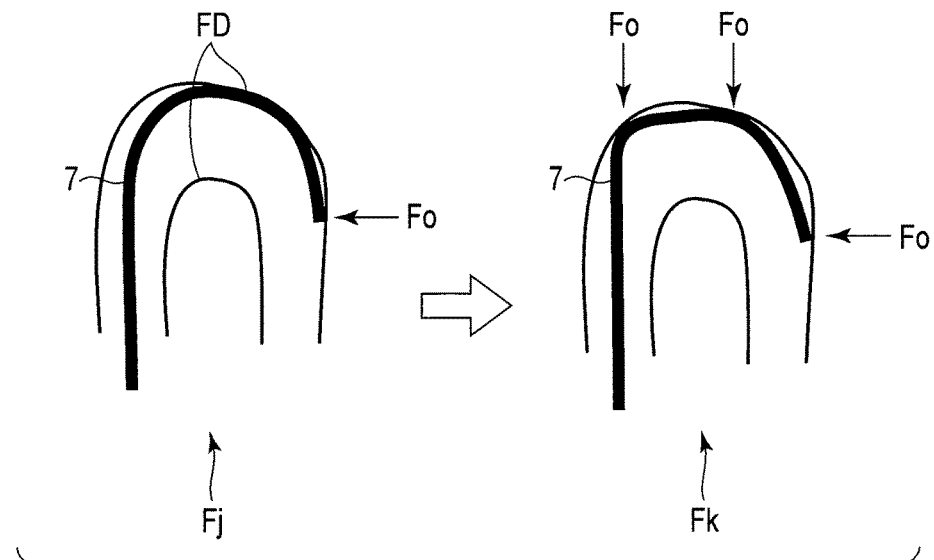
FIG. 24 is an illustration of an operation of an observation target object load estimation circuit.

First, it is assumed that the insertion section 7 is deformed from the j-th insertion section shape information Fj to the k-th insertion section shape information Fk as shown in FIG. 24. The insertion section 7 roughly maintains its linear shape when a load is not applied thereto from the outside. If the insertion section 7 takes the j-th insertion section shape information Fj, its distal-end portion 7a contacts the observation target object 2 and thus receives pushing force FO, with the result that it is bent as shown on the left side of FIG. 24.

When the operator manipulates the insertion section 7 further in a pushing direction, the insertion section 7 takes the k-th insertion section shape information Fk. At this time, the insertion section 7 contacts the observation target object 2 in at least three positions.

The load estimator 60 performs an appropriate arithmetic operation using information such as flexibility of the insertion section 7 and pushing force required for the flexibility, which is stored in the information storage 35 in the support information circuit 22, to estimate the pushing force of the insertion section 7 applied to the observation target object 2 as a reaction force of the obtained pushing force. The observation target object load information KG estimated by the load estimator 60 is stored in the information storage 35.

In addition, even though the inner profile of the observation target object 2 is deformed and moved like a living body, the load estimator 60 can estimate the pushing force applied to the observation target object 2 in the same manner if the information storage 35 stores information such as deformation easiness of the observation target object 2 and pushing force required for the deformation.

At that time, the load estimator 60 can estimate a direct manipulation that influences the pushing force FO by making use of information of the type, direction and amount of the manipulation which is the operator manipulation information from the manipulation estimator 34. It is thus possible to improve the accuracy of the value of the pushing force FO and its influence.

Moreover, the load estimator 60 can also combine the insertion section future shape information M. Even though the insertion section future shape information M is used, the basic operation of the load estimator 60 remains unchanged. By using this information, the pushing force to be loaded on the observation target object 2 with the future timing can be known in advance.

As in the first modification to this embodiment, the pushing force FO or the like, which is applied to the observation target object 2, can be estimated by estimating a load (pushing force FO) applied to the observation target object 2. Accordingly, a load on the observation target object 2 can be evaluated qualitatively or quantitatively in the past, at the present time and in the future. Furthermore, when the observation target object 2 is a living body, it is possible to estimate a patient's pain, fear of damage to an organ, etc., and the medical endoscope can reduce a patient's load and the risk of damage to an organ or the like.

Like in the foregoing first embodiment, the advantages that time required for operator's training and skill improvement is made shorter than in the conventional endoscope system and even an inexperienced or low skill level operator can insert and remove the endoscope relatively easily, can be expected.

Fourth Embodiment

A fourth embodiment of the present invention will be described below with reference to the drawings. In this embodiment, the sections common to those of the first to third embodiments will not be described but only different sections will be described in detail.

This embodiment differs from the above first to third embodiments in that the manipulation estimator 34 functions as a future manipulation estimator to estimate future operator manipulation information. The manipulation estimator 34 will be described below, reading it as a future manipulation estimator 34.

In the first and second embodiments, the manipulation estimator 34 estimates an operator's manipulation that has been performed until the past or the present time on the basis of the insertion section shape information F. The future shape estimator 33 estimates advance (future) insertion section shape information M assuming only the case where the operator's manipulation that has been performed until the past or the present time continues as it is.

In contrast, the future manipulation estimator 34 of this embodiment estimates a future operator's manipulation that could be performed by the operator in the future and outputs it to the future shape estimator 33. The configurations and functions other than the future manipulation estimator 34 are basically common to those of the first to third embodiments.

[Operation of Future Manipulation Estimator 34]

The operator manipulation information estimation circuit 34 estimates the operator manipulation information L by the operation described in the foregoing first embodiment. This operator manipulation information L is information about the operator's manipulation that has been performed until the past or the present time. The operator manipulation information L includes information of the type of manipulation, the direction of manipulation and the amount of manipulation.

The future manipulation estimator 34 receives the above operator manipulation information L to estimate is future operator manipulation information L (=LF) indicating a future operator's manipulation. The future manipulation estimator 34 also receives shape change information KA included in the operator manipulation information estimation circuit 34 to estimate future operator manipulation information LF using the information KA.

The operator's manipulation includes three basic manipulations of a first manipulation of inserting/removing the insertion section 7 into/from the internal space 3 of the observation target object 2 like an insertion/removal manipulation, a second manipulation of rotating the insertion section 7 on its axis like a rotation/twist operation, and a third manipulation of manipulating a bending portion by the control handle 11 like a bending manipulation. In other words, as a manipulation type, there are three manipulations of a first manipulation of insertion/removal, a second manipulation of rotation/twist, and a third manipulation of bending. These manipulations can be performed independently or simultaneously.

Between an operator's manipulation at a certain timing and an operator's manipulation at the next timing, there are three manipulations of continuation, stop and reversal (the manipulations are the same but their directions are opposite to each other) in terms of the type and direction of manipulation.

The future manipulation estimator 34 estimates the type and direction of operator's manipulation L input from the manipulation estimator 34 in consideration of three possibilities of continuation, stop and reversal.

The future manipulation estimator 34 also estimates the amount of manipulation in consideration of three possibilities of continuation (continues the same amount), increase in amount and decrease in amount. If the amount of manipulation is zero, the manipulation is stopped. The stop of manipulation when the amount of manipulation is zero is the same as stop that is considered in terms of the type and direction of manipulation and thus the amount of manipulation is considered as zero.

Based on the above, the future manipulation estimator 34 estimates a future operator's manipulation assuming the following three patterns for the type and direction of manipulation. As the operator's manipulation, a simple manipulation and a combination of simple manipulations can be considered. For example, in a complex manipulation such as that the insertion section is twisted while being inserted, the following first to fourth future operator's manipulations are estimated as candidates for each of the insertion and twist operations.

(1) First Future Operator's Manipulation

In this manipulation, it is estimated that the type, direction and amount of manipulation that has been performed until the past or the present time are continued as they are. The future manipulation estimator 34 receives the operator manipulation information L from the manipulation estimator 34 and outputs it to the future shape estimator 33 as it is.

(2) Second Future Operator's Manipulation

In this manipulation, it is estimated that the manipulation that has been performed until the past or the present time is stopped.

(3) Third Future Operator's Manipulation

In this manipulation, it is estimated that the direction of manipulation is reversed while maintaining the type of manipulation.

(4) Fourth Future Operator's Manipulation

In this manipulation, it is estimated that a manipulation that is not currently performed is newly started.

In the second future operator manipulation, information of the amount of manipulation is always zero because the manipulation is stopped. In the fourth future operator's manipulation, the amount of manipulation always increases. Furthermore, in the third future operator's manipulation, the amount of manipulation always decreases because the direction of manipulation is reversed and thus the amount of manipulation decreases and then increases in the reverse direction, or in the negative direction.

As described above, the number of alternatives for the manipulation amount corresponding to the first to fourth future operator's manipulations can be reduced.

The future manipulation estimator 34 estimates future operator manipulation information L (=LF) based on one or more items of operator manipulation information including the latest operator's manipulation.

The future manipulation estimator 34 estimates which one of the first to fourth future operator's manipulations is to be performed.

First, when the future manipulation estimator 34 can determine that the operator continuously performs the same manipulation and steadily proceeds to insert/remove the insertion section 7 into/from the observation target object 2 by the shape change information KA, or when the direction and amount of the operator's manipulation are substantially equal to those of movement of the insertion section 7, the future manipulation estimator 34 determines that there is a strong possibility that the same operation continues. In other words, the future manipulation estimator 34 estimates that there is a strong possibility that a first future operator's manipulation is performed.

On the other hand, when the future manipulation estimator 34 can determine that the operator frequently changes his or her manipulation and does not smoothly proceed to insert/remove the insertion section 7 into/from the observation target object 2 by the shape change information KA, for example, when the direction and amount of movement of the insertion section 7, especially its distal end portion, differs from those of the operator's manipulation or when the insertion section 7 hardly moves, the future manipulation estimator 34 estimates that there is a low possibility that the same operation continues and there is a strong possibility that the manipulation stops and then the next manipulation is performed in a different direction. In other words, the future manipulation estimator 34 estimates that the third and fourth future operator's manipulations are performed after the second future operator's manipulation is performed.

If, furthermore, the same operator's manipulation continuous over a long time and a fixed period or longer, especially, the manipulation amount decreases gradually, it is considered that an object of the manipulation can be attained. Accordingly, the future manipulation estimator 34 estimates that the third and fourth future operator's manipulations are performed after the second future operator's manipulation is performed.

When the same manipulation continues, the future manipulation estimator 34 estimates that there is a strong possibility that the amount of manipulation increases if the manipulation is performed for a given time or shorter. The future manipulation estimator 34 estimates that there is a strong possibility that the amount of manipulation remains or decreases if the manipulation continues for a given time or longer. Similarly, when the third or fourth future operator's manipulation is performed, the future manipulation estimator 34 estimates that the amount of manipulation always increases and that there is a low possibility that the amount of manipulation becomes very large suddenly.

Furthermore, when the operator's operation time itself is long (usually this information can be used because the endoscope system includes a clock and is able to manage the operation time), the future manipulation estimator 34 estimates a future operator's manipulation using circumstances information, such as that a removal-direction manipulation is very likely to be performed.

Furthermore, the future manipulation estimator 34 analyzes, e.g. a manipulation that is very likely to be performed subsequently to a certain manipulation, for each of the observation target object 2, operator, endoscope apparatus and the like, from, e.g. analysis results of the past support information log when the observation target object 2 was observed, and estimates future operator manipulation information using the analysis results. The support information log described here is a system in which in the operation of the insertion/removal system using the support information circuit 22, different items of information received and generated by the respective sections are stored in the information storage and an operator can confirm later what operation or manipulation is performed.

The support information log allows only a necessary log to be extracted according to its purpose and allows the procedure of insertion manipulation, the success or failure of the insertion/removal, etc. to be analyzed. The support information log includes a memory signally connected to each circuit and a data processing program for calling the memory which are provided in the support information circuit 22 and. The support information circuit 22 is also able to display the support information log on the display.

In the case of the future operator's manipulation, it is difficult to estimate the amount of manipulation accurately. It is therefore favorable to configure the system to retain a standard manipulation amount as a default value in the manipulation and output it. The default value can be set referring to the value of the support information log and corrected appropriately from that value.

In the above example, a future operator's manipulation is estimated for each of the three basic manipulations of insertion/removal manipulation, rotation/twist manipulation and bending manipulation, but there is a combined manipulation to perform these manipulations in complexity. For example, the insertion section may be inserted/removed while being twisted. Though this combination is theoretically possible, a manipulation such as that the insertion section is bent as well as twisted while being inserted, is extremely rare in the actual operation.

Furthermore, the manipulations are generally performed alone rather than in combination. Therefore, when the future manipulation estimator 34 determines that the manipulations are very likely to be performed in combination, such as the case where it estimates information from the operator's support information log, a specific medical procedure or the like, it estimates future operator information in consideration of the manipulations performed in combination. The estimated future operator information is stored in the information storage.

The future manipulation estimator 34 also has a function of outputting a plurality of items of future operator manipulation information L (=LF) in parallel to the future shape estimator 33. Since the future operator manipulation information L (=LF) is not for the actual operator's manipulation, the operator is likely to perform different manipulations. If, therefore, the items of future operator manipulation information L (=LF) are output to the future shape estimator 33 in the descending order of possibility that insertion section future shapes may be taken, the future shape estimator 33 can estimate the insertion section future shapes. At this time, the future manipulation estimator 34 considers various information items and situations as described above, sequences the items of future operator manipulation information L (=LF) in the order that an insertion section future shape may be taken, and outputs them to the future shape estimator 33 in that order. If the sequencing is difficult or information is short, the foregoing first future operator manipulation information is output and then the second, third and fourth future operator manipulation information L (=LF).

In response to this, the future shape estimator 33 estimates a future shape of the insertion section 7 based on all the input future operator manipulation information L (=LF). The future operator manipulation information L (=LF) is the same type information as the operator manipulation information L. For this reason, the future shape estimator 33 performs the same operation for the future operator manipulation information L (=LF) as that for the operator manipulation information L.

The configuration of this embodiment makes it possible to estimate a future shape of the insertion section 7 which may be taken with the next timing and display and provide it for the operator as insertion manipulation support information. Consequently, it is possible to expect the advantages that time required for operator's training and skill improvement is made shorter than in the conventional endoscope system and even an inexperienced or low skill level operator can insert and remove the endoscope relatively easily.

As in this embodiment, it is particularly possible to estimate a manipulation to be performed by the operator as future operator manipulation information L (=LF), estimate an insertion section future shape based on this information L (=LF), and derive a possible shape variation of a future shape of the insertion section 7 and provide it for the operator. In addition, for example, each individual insertion section future shape can be estimated except for the continuation of the current manipulation, and it is possible to provide information effective for the operator.

The present invention is not limited to the foregoing embodiments.

The shape sensor 8 is not limited to the optical fiber sensor.

As the shape sensor 8, any sensor can be used if it can detect the shape of the insertion section 7 inside the observation target object 2. For example, a plurality of magnetic coils can be arranged in the insertion section 7 and a magnetic antenna can be disposed outside the insertion section 7. In this case, the absolute position of the antenna can be confirmed and thus any insertion amount sensor need not be used as described below.

An X-ray camera can be used. In the case of medical endoscopes, a procedure for confirming a shape of the insertion section 7 in a living body and a relative position between the living body and the insertion section 7 by an X-ray camera has been known for a long time. In this case, the position and shape of an organ in the living body can be confirmed roughly and accordingly the inner profile of the observation target object 2 can be improved in precision and accuracy. In the case of X-ray cameras, if only one X-ray camera, only two-dimensional data is obtained. This case can be handled by processing the above-described configuration and operations two-dimensionally. As compared with three-dimensional information, the amount of information is reduced, but a fixed effect can be expected.

Figure 25:
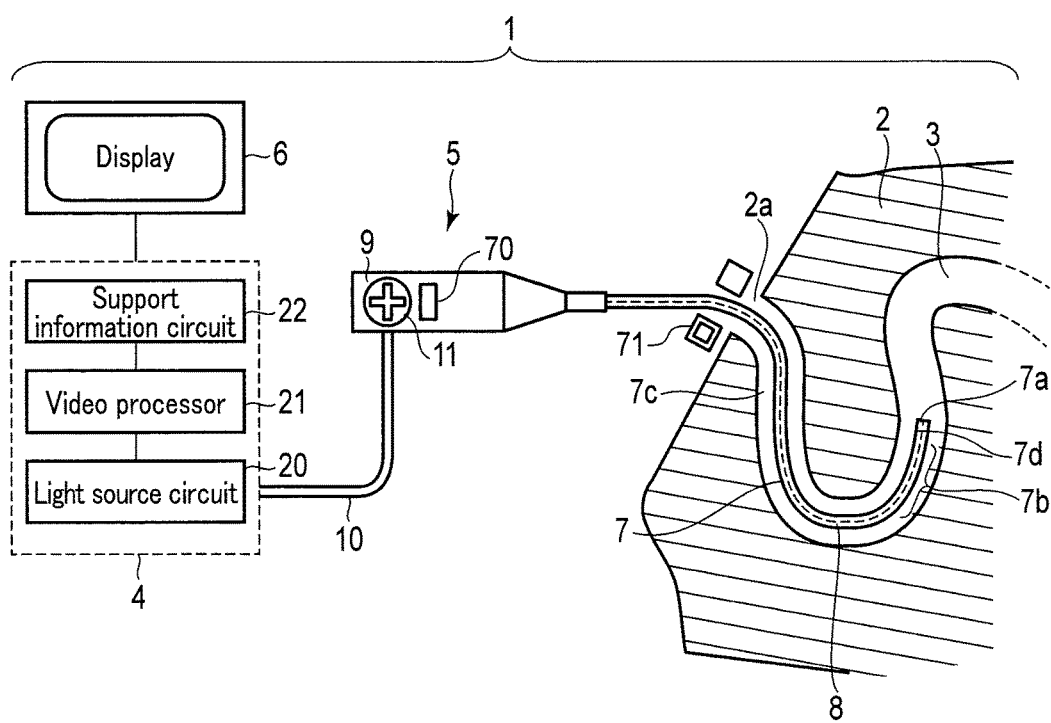
FIG. 25 is a configuration diagram showing an example of a modification to the present invention.

Furthermore, in all the embodiments described above, a sensor loaded onto the endoscope is directed to only the optical fiber sensor 8 as a shape sensor. Without limiting to this, for example, as shown in FIG. 25, a manipulation amount sensor 70 capable of directly detecting the manipulation amount of the control handle 11 to detect a bending manipulation of the active bending portion 7b of the endoscope is disposed and an insertion amount sensor 71 capable of detecting the direction and amount of insertion/removal manipulation of the insertion section 7 is disposed at the insertion opening 2a of the observation target object 2, and the manipulation amount sensor 70 and the insertion amount sensor 71 can be combined. By using the outputs from these sensors 70 and 71, part of the estimation performed by the manipulation estimator 34 can be detected directly.

Since, furthermore, the future manipulation estimator 34 estimates future operator manipulation information using results output from the manipulation amount sensor and the insertion amount sensor, the future operator manipulation information can be improved in its accuracy and precision.

Furthermore, the foregoing embodiments are directed to an example of replacing different sections. Without limiting to this, for example, the functions of the change deriving circuit 32 from the first embodiment through the modification to the second embodiment can be incorporated into one insertion section time change deriving circuit and can be selected when it is used, or an appropriate procedure can automatically be selected according to the situation. Similarly, the configurations of all of the foregoing embodiments can be included in one insertion/removal system to select one of the functions and estimate and display it at the same time.

In the foregoing embodiments and their modifications, an endoscope is exemplified as a subject matter; however, the present invention is not limited to the endoscope. The present invention is favorable for all insertion/removal systems to perform a desired operation by inserting the flexible insertion section 7 into a tube hole. For example, treatment instruments and forceps to be inserted into the forceps channel of an endoscope for treatment, catheters to be inserted into blood vessels and lymphatic vessels for various treatments, various industrial observation/repair devices for maintenance of industrial piping, etc. are particularly favorable for the systems. Some of the insertion/removal systems may not have the function of performing an active manipulation and, in that case, the operator manipulation information L does not include "a bending manipulation" but the object can be attained by almost the same procedure, operation and function as described above.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A future shape estimation apparatus comprising:
   an insertion section with flexibility which is to be inserted into an observation target object;
   a shape sensor which detects a bending state of the insertion section and outputs a detection signal; and
   a computer processor configured to:
      calculate insertion section shape information of the insertion section based on the detection signal output from the shape sensor;
      compare the insertion section shape information calculated at different times and derive shape time change information indicating a shape change of the insertion section based on a result of the comparison; and
      estimate a future shape of the insertion section a predetermined lapse of time after a present time based on the insertion section shape information calculated and the shape time change information derived, and output the future shape as future estimation shape information.

2. The future shape estimation apparatus according to claim 1,
   wherein the insertion section includes an endoscope insertion section to observe an inner surface of the observation target object.

3. The future shape estimation apparatus according to claim 1, further comprising:
   a shape sensor controller which outputs first to n-th timing signals indicative of timing of detection of a shape of the insertion section to the shape sensor when n is a natural number of two or more, j and k are different natural numbers of n or less, and j is smaller than k (j<k),
   wherein the computer processor is configured to:
      calculate j-th insertion section shape information and k-th insertion section shape information based on the detection signal output from the shape sensor to correspond to a j-th timing signal and a k-th timing signal included in the first to n-th timing signals; and
      compare the j-th insertion section shape information and the k-th insertion section shape information calculated to derive the shape time change information of the insertion section from when the j-th timing signal is output until the k-th timing signal is output.

4. The future shape estimation apparatus according to claim 3,
   wherein the computer processor is configured to:
      compare the j-th insertion section shape information and the k-th insertion section shape information to extract a shape changing region in which the insertion section is changed;
      derive at least one of a type, a direction and an amount of a shape change of the insertion section in the shape changing region; and
      output a derived one thereof as the shape time change information of the insertion section.

5. The future shape estimation apparatus according to claim 3,
   wherein the computer processor is configured to:
      compare the j-th insertion section shape information and the k-th insertion section shape information to extract one or more shape unchanging regions in which the insertion section is not changed;
      derive at least one of a type, a direction and an amount of a shape change of the insertion section based on a change of a relative positional relationship between the shape unchanging regions; and
      output a derived one thereof as the shape time change information of the insertion section.

6. The future shape estimation apparatus according to claim 1,
   wherein the computer processor is configured to:
      estimate manipulation information including a manipulation of inserting the insertion section into the observation target object based on the shape time change information of the insertion section; and
      estimate the future estimation shape information based on the manipulation information.

7. The future shape estimation apparatus according to claim 6, further comprising:
   a shape sensor controller which outputs first to n-th timing signals indicative of timing of detection of a shape of the insertion section to the shape sensor when n is a natural number of two or more, j and k are different natural numbers of n or less, and j is smaller than k (j<k),
   wherein the computer processor is configured to:
      calculate j-th insertion section shape information and k-th insertion section shape information based on the detection signal output from the shape sensor to correspond to a j-th timing signal and a k-th timing signal included in the first to n-th timing signals output;
      compare the j-th insertion section shape information and the k-th insertion section shape information calculated to derive the shape time change information of the insertion section from when the j-th timing signal is output until the k-th timing signal is output; and
      assume that a shape change of the insertion section is made by an insertion manipulation of the insertion section to estimate at least one of a type, a direction and an amount of the shape change of the insertion section during a period from when the j-th timing signal is generated until the k-th timing signal is generated.

8. The future shape estimation apparatus according to claim 3,
wherein the computer processor is configured to:
estimate at least part of inner profile information indicating shape information of an inner surface of the observation target object based on the shape time change information; and
estimate the future estimation shape information based on the inner profile information of the observation target object.

9. The future shape estimation apparatus according to claim 6,
wherein the processor is configured to:
estimate information of future manipulation of the insertion section to be performed based on the manipulation information; and
estimate a future shape of the insertion section when the information of future manipulation is estimated.

10. The future shape estimation apparatus according to claim 1,
wherein the shape sensor is loaded onto the insertion section and includes one of an optical fiber sensor and a magnetic sensor.

11. The future shape estimation apparatus according to claim 1,
wherein the shape sensor includes one of an X-ray camera and an external camera.

12. The future shape estimation apparatus according to claim 6, further comprising:
a control handle which allows a shape of the insertion section to be manipulated; and
a manipulation amount sensor which detects a manipulation amount of the control handle,
wherein the computer processor is configured to estimate the manipulation information for the insertion section based on the manipulation amount of the control handle detected by the manipulation amount sensor.

13. The future shape estimation apparatus according to claim 6, further comprising:
an insertion amount sensor provided at an entrance portion through which the insertion section is inserted into the observation target object to detect an insertion amount of the insertion section inserted into the observation target object,
wherein the computer processor is configured to estimate the manipulation information for the insertion section based on the insertion amount of the insertion section detected by the insertion amount sensor.

14. The future shape estimation apparatus according to claim 1, further comprising an information storage which stores the estimated future estimation shape information and which allows the future estimation shape information to be read when necessary.

15. An insertion/removal system comprising
an insertion section with flexibility which is to be inserted into an observation target object;
a shape sensor which detects a bending state of the insertion section and outputs a detection signal;
a control section which performs a bending manipulation of the insertion section; and
a computer processor configured to:
calculate insertion section shape information of the insertion section based on the detection signal output from the shape sensor;
compare the insertion section shape information calculated at different times and derive shape time change information indicating a shape change of the insertion section based on a result of the comparison; and
estimate a future shape of the insertion section a predetermined lapse of time after a present time based on the insertion section shape information calculated and the shape time change information derived, and output the future shape as future estimation shape information.

16. An insertion/removal system comprising:
an insertion section with flexibility which is to be inserted into an observation target object;
a shape sensor which detects a bending state of the insertion section and outputs a detection signal;
a control section which bends the insertion section; and
a computer processor configured to:
calculate insertion section shape information of the insertion section based on the detection signal output from the shape sensor;
compare the insertion section shape information calculated at different times and derive shape time change information indicating a shape change of the insertion section based on a result of the comparison;
estimate a future shape of the insertion section a predetermined lapse of time after a present time based on the insertion section shape information calculated and the shape time change information derived, and output the future shape as future estimation shape information; and
notify future estimation shape information output to support insertion/removal of the insertion section into/from the observation target object.

17. A future shape estimation method comprising:
detecting a bending state of a flexible insertion section to be inserted into an observation target object by a shape sensor and outputting a detection signal;
calculating insertion section shape information of the flexible insertion section based on the detection signal;
comparing the insertion section shape information calculated at different times and deriving shape time change information indicating a shape change of the flexible insertion section based on a result of the comparison; and
estimating a future shape of the insertion section a predetermined lapse of time after a present time based on the insertion section shape information and the shape time change information, and outputting the future shape as future estimation shape information.

18. A recording medium non-transitory storing a future shape estimation program which causes a computer to perform:
a receiving function of receiving a detection signal output from a shape sensor which detects a bending state of a flexible insertion section inserted into an observation target object;
an insertion section shape calculation function of calculating insertion section shape information of the flexible insertion section based on the detection signal;
a shape time change deriving function of comparing the insertion section shape information calculated at different times and deriving shape time change information indicating a shape change of the flexible insertion section based on a result of the comparison; and
an insertion section future shape estimation function of estimating a future shape of the flexible insertion section a predetermined lapse of time after a present time based on the insertion section shape information and the shape time change information, and outputting the future shape as future estimation shape information.

\* \* \* \* \*

UNITED STATES PATENT AND TRADEMARK OFFICE
CERTIFICATE OF CORRECTION

PATENT NO. : 10,765,299 B2
APPLICATION NO. : 15/627687
DATED : September 8, 2020
INVENTOR(S) : Takeshi Ito Page 1 of 1

It is certified that error appears in the above-identified patent and that said Letters Patent is hereby corrected as shown below:

On the Title Page

(73) Assignee should read:
OLYMPUS CORPORATION, Tokyo (JP)

Signed and Sealed this
Twelfth Day of January, 2021

Andrei Iancu
*Director of the United States Patent and Trademark Office*